(12) United States Patent
Kondis

(10) Patent No.: US 12,678,040 B2
(45) Date of Patent: *Jul. 14, 2026

(54) MULTI-CHANNEL SUBJECTIVE REFRACTOR

(71) Applicant: RxSight, Inc., Aliso Viejo, CA (US)

(72) Inventor: John Kondis, Irvine, CA (US)

(73) Assignee: RxSight, Inc., Aliso Viejo, CA (US)

( * ) Notice: Subject to any disclaimer, the term of this patent is extended or adjusted under 35 U.S.C. 154(b) by 247 days.

This patent is subject to a terminal disclaimer.

(21) Appl. No.: 18/734,155

(22) Filed: Jun. 5, 2024

(65) Prior Publication Data

US 2025/0375105 A1     Dec. 11, 2025

(51) Int. Cl.
| | |
|---|---|
| *A61B 3/02* | (2006.01) |
| *A61B 3/00* | (2006.01) |
| *A61B 3/028* | (2006.01) |
| *A61B 3/10* | (2006.01) |
| *A61B 3/12* | (2006.01) |

(52) U.S. Cl.
CPC .......... *A61B 3/0285* (2013.01); *A61B 3/0058* (2013.01)

(58) Field of Classification Search
CPC ......... A61B 3/02; A61B 3/102; A61B 3/1025; A61B 3/113; A61B 3/1015; A61B 3/1225; A61B 3/024; A61B 3/06; A61B 3/032; A61B 3/005; G02B 27/01; G02B 27/00; G02B 27/0149; G02B 27/1006
USPC ....... 351/200, 205, 206, 209, 210, 221–223, 351/237–240, 245, 246; 359/629, 630, 359/632, 634
See application file for complete search history.

(56) References Cited

U.S. PATENT DOCUMENTS

| | | |
|---|---|---|
| 7,131,727 B2 | 11/2006 | Jones et al. |
| 7,455,403 B2 | 11/2008 | Jones et al. |
| 7,963,654 B2 | 6/2011 | Aggarwala |
| 8,911,084 B2 | 12/2014 | Fernandez Martinez et al. |
| 8,985,768 B2 | 3/2015 | Lai et al. |
| 9,681,800 B2 | 6/2017 | Schwiegerling et al. |

(Continued)

FOREIGN PATENT DOCUMENTS

WO     2022/236333 A2     11/2022

OTHER PUBLICATIONS

Alarcon, et al., "Optical bench evaluation of the effect of pupil size in new generation monofocal intraocular lenses", BMC Ophthalmology, (2023) 23:112, https://doi.org/10.1186/s12886-023-02839-y, 8 pages.

(Continued)

*Primary Examiner* — Dawayne Pinkney

(57)     ABSTRACT

A multi-channel subjective refractor can comprise a first display to generate a first image; a second display to generate a second image; a first channel to refract the first image with a first channel refraction; a second channel to refract the second image with a second channel refraction; a beam combiner to receive and to combine the first image and the second image; and a shared channel, to receive the first image and the second image from the beam combiner to refract, in combination with the first channel, the first image with a first refraction; to refract, in combination with the second channel, the second image with a second refraction; and to present the first image with the first refraction and the second image with the second refraction to an eye simultaneously.

20 Claims, 15 Drawing Sheets

(56)                    References Cited

U.S. PATENT DOCUMENTS

| 2015/0313463 | A1* | 11/2015 | Trumm | ................. | A61B 3/103 |
| | | | | | 351/246 |
| 2018/0161231 | A1 | 6/2018 | Tse et al. | | |
| 2019/0265472 | A1* | 8/2019 | Sugiyama | .......... | G02B 27/0101 |
| 2021/0338077 | A1 | 11/2021 | Sapiens et al. | | |
| 2023/0004005 | A1* | 1/2023 | Uhlendorf | .......... | G02B 27/0172 |

OTHER PUBLICATIONS

Fűlep, et al., "Application of Correlation-Based Scoring Scheme for Visual Acuity Measurements in the Clinical Practice", Trans Vis Sci Tech, (2019), 8(2):19, https://doi.org/10.1167/tvst.8.2.19, 13 pages.
Fűlep, et al., "Simulation of visual acuity by personalizable neuro-physiological model of the human eye", Scientific Reports, (2019), 9:7805, https://doi.org/10.1038/s41598-019-44160-z, 15 pages.
Leube, et al., "Individual neural transfer function affects the prediction of subjective depth of focus", Scientific Reports, (2018) 8:1919, DOI: 10.1038/s41598-018-20344-x, 8 pages.
Palomino-Bautista, et al., "Depth of field measures in pseudophakic eyes implanted with different type of presbyopia-correcting IOLS", Scientific Reports, (2021) 11:12081, https://doi.org/10.1038/s41598-021-91654-w, 8 pages.
Rodriguez-Lopez, et al., "The Direct Subjective Refraction: Unsupervised measurements of the subjective refraction using defocus waves", bioRxiv, (Dec. 6, 2021), https://doi.org/10.1101/2021.12.04.471123, 27 pages.
Rodriguez-Lopez, et al., "Robustness of the Direct Subjective Refraction method", Arvo Annual Meeting Abstract, Jun. 2023, 3 pages.

* cited by examiner head-mounted
binocular multi-channel
subjective refractor 100h binocular multi-channel
subjective refractor 100b right multi-channel
refractor 100R left multi-channel
refractor 100L a method 200 of
operating a multi-channel
subjective refractor

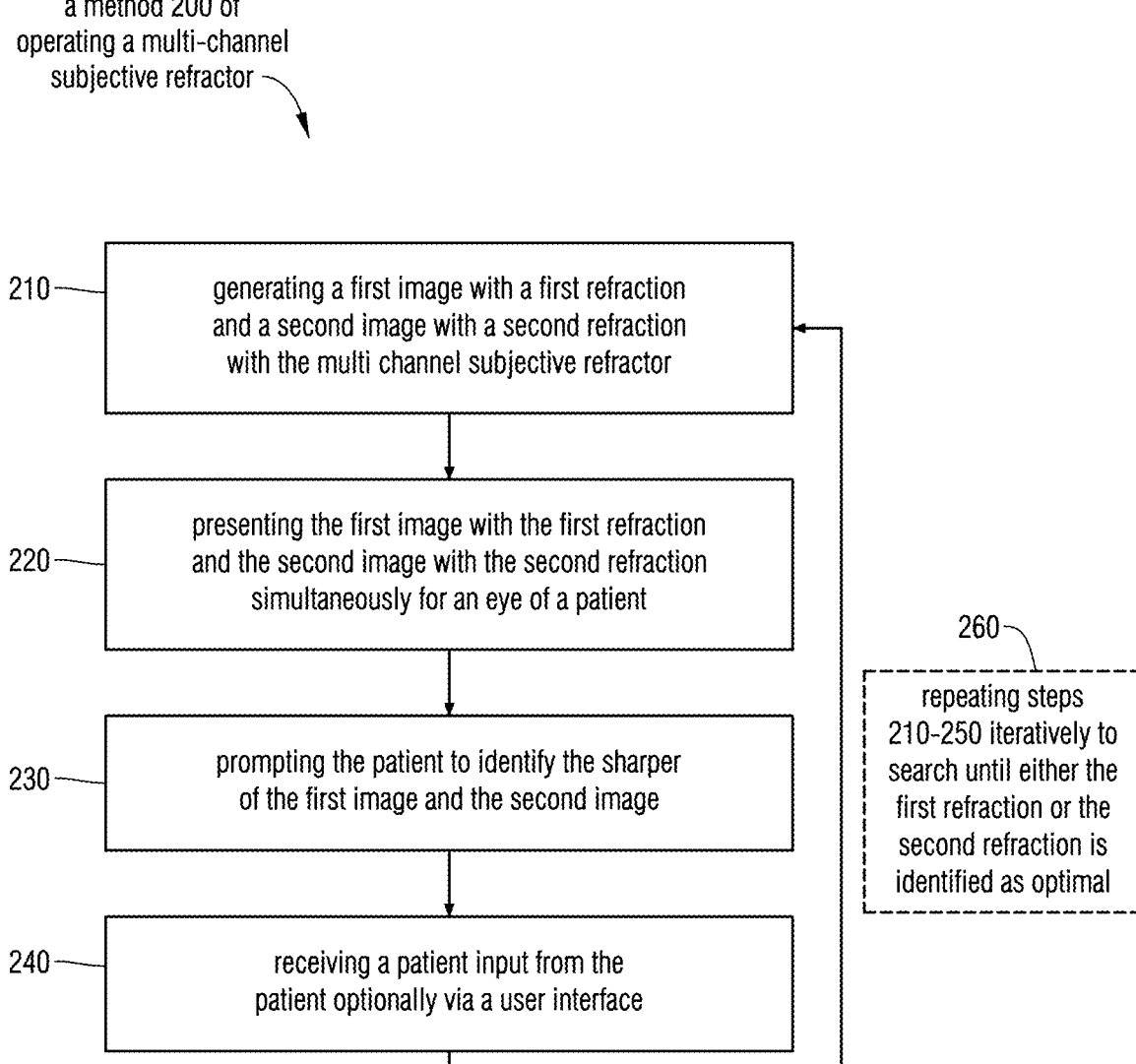

210 — generating a first image with a first refraction
and a second image with a second refraction
with the multi channel subjective refractor 220 — presenting the first image with the first refraction
and the second image with the second refraction
simultaneously for an eye of a patient 230 — prompting the patient to identify the sharper
of the first image and the second image 240 — receiving a patient input from the
patient optionally via a user interface 250 — changing at least one of the first refraction and the
second refraction in response to the patient input
via a multi-channel subjective refractor controller 260 — repeating steps
210-250 iteratively to
search until either the
first refraction or the
second refraction is
identified as optimal

FIG. 8 generating 210

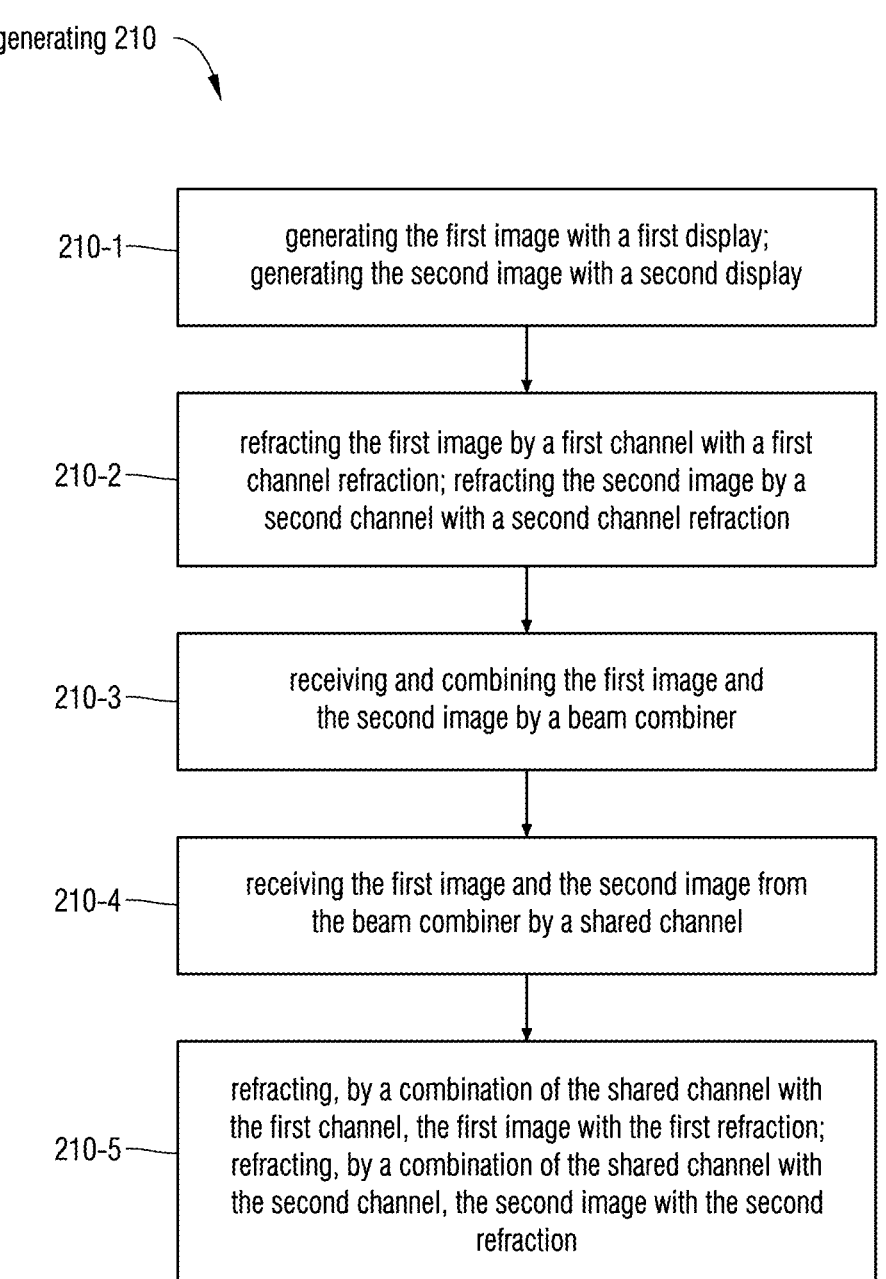

210-1 — generating the first image with a first display; generating the second image with a second display 210-2 — refracting the first image by a first channel with a first channel refraction; refracting the second image by a second channel with a second channel refraction 210-3 — receiving and combining the first image and the second image by a beam combiner 210-4 — receiving the first image and the second image from the beam combiner by a shared channel 210-5 — refracting, by a combination of the shared channel with the first channel, the first image with the first refraction; refracting, by a combination of the shared channel with the second channel, the second image with the second refraction

FIG. 9

MULTI-CHANNEL SUBJECTIVE REFRACTOR

TECHNICAL FIELD

This application is related to refractors, in more detail, to multi-channel, parallel-presenting subjective refractors.

BACKGROUND

Refractors, or phoropters, have been employed by optometrists for a very long time for the purpose of determining the optimal vision correction for their patients. The historical refractor is an opto-mechanical system where the optometrist can change lenses of differing diopters in and out of the patient's viewing path of an eye chart sequentially and prompt the patient to report which lens provided the sharper image, the previous or the present one. Such refractors that rely on feedback from the patient can be classified as subjective refractors.

With recent technical developments, it became possible to perform objective measurements of the wavefronts of the patients' eyes by various techniques, using opto-electronic aberrometers from companies like NIDEK, WaveDyn, or many other providers. One motivation for introducing objective aberrometers was the belief that such measurements can be automated and therefore may eliminate the need for a trained optometric technician or the optometrist, thus saving precious time and cost. Another motivation was the belief that the high precision measurements of these aberrometers may determine the optimal refraction better and more reproducibly than "unreliable" subjective patient feedback. Much to the surprise of practitioners, however, objective aberrometers suffer from a frequent disagreement between the best refraction identified from the objective physical wavefront measurements and the subjectively best refractive condition reported by the patient. Therefore, there is an ongoing role for subjective refractors in an optometrist's practice. Remarkably, in spite of all the developments in opto-electronics, today's refractors/phoropters look startlingly close to the refractors used several decades ago, even a century ago. Puzzlingly, there has been minimal progress to apply the techniques of modern electro-optical devices to create new generations of phoropters, and to improve their performances.

SUMMARY

In order to adapt some advantages and benefits of the modern opto-electronic devices for the present-day phoropter technologies, a multi-channel subjective refractor has been developed. Some embodiments of this multi-channel subjective refractor can comprise a first display to generate a first image; a second display to generate a second image; a first channel to refract the first image with a first channel refraction; a second channel to refract the second image with a second channel refraction; a beam combiner to receive and to combine the first image and the second image; and a shared channel, to receive the first image and the second image from the beam combiner to refract, in combination with the first channel, the first image with a first refraction; to refract, in combination with the second channel, the second image with a second refraction; and to present the first image with the first refraction and the second image with the second refraction to an eye simultaneously.

In some embodiments, a method of operating a multi-channel subjective refractor, the method comprises the steps of generating a first image with a first refraction and a second image with a second refraction with the multi-channel subjective refractor; presenting the first image with the first refraction and the second image with the second refraction simultaneously for an eye of a patient; and prompting the patient to identify the sharper of the first image and the second image.

BRIEF DESCRIPTION OF THE DRAWINGS

FIG. 8 shows steps of a method of using a multi-channel subjective refractor.

FIG. 9 shows sub-steps of the generating step.

DETAILED DESCRIPTION

In traditional refractors, or phoropters, the patient is shown an eye chart with a first and a second refraction sequentially, and is prompted to choose/report the refraction that provided a sharper image: "Which was sharper: one or two"? However, to answer this prompt, the patient must remember the visual quality of the previously shown refraction which is now not visible. Therefore, these sequential refractor designs and processes put a substantial mental and cognitive demand on the patient: an unwanted feature of any medical process. Second, for a large fraction of patients, especially older patients, the sequential presentation often leads to the patient asking the optometrist several times to flip back and forth between the refractions. This back-and-forth can be quite frustrating for all involved. Third, sequential processes are time consuming and use an excessive amount of the very precious chair time of the optometrist, thus being quite costly in time and money. Fourth and finally, in spite of all of this effort and cost, since the patient does not see the two, compared images simultaneously, the selection process still may not converge and select the optimal refraction.

A notable differentiator of a here-disclosed multi-channel subjective refractor 100 is that it presents the images with the to-be compared refractions simultaneously, side-by-side, or top-bottom. Such a simultaneous, or multi-channel presentation of refractions instantaneously eliminates the demand that the patient remembers the appearance of the previous image, and therefore removes the accompanying mental load, to the great relief of patient and optometrist alike. Second, comparing two images with both of them visible at the same time naturally eliminates the frustrating back-and-forth ("Which is sharper: one or two?") with the optometrist. Third, such a simultaneous presentation saves very valuable chair time and allows the optometrist to see many more patients a day, and thus reduces cost and increases revenue. Fourth and finally, the process leads to the determination of the optimal refraction with a higher probability.

Figure 1A:
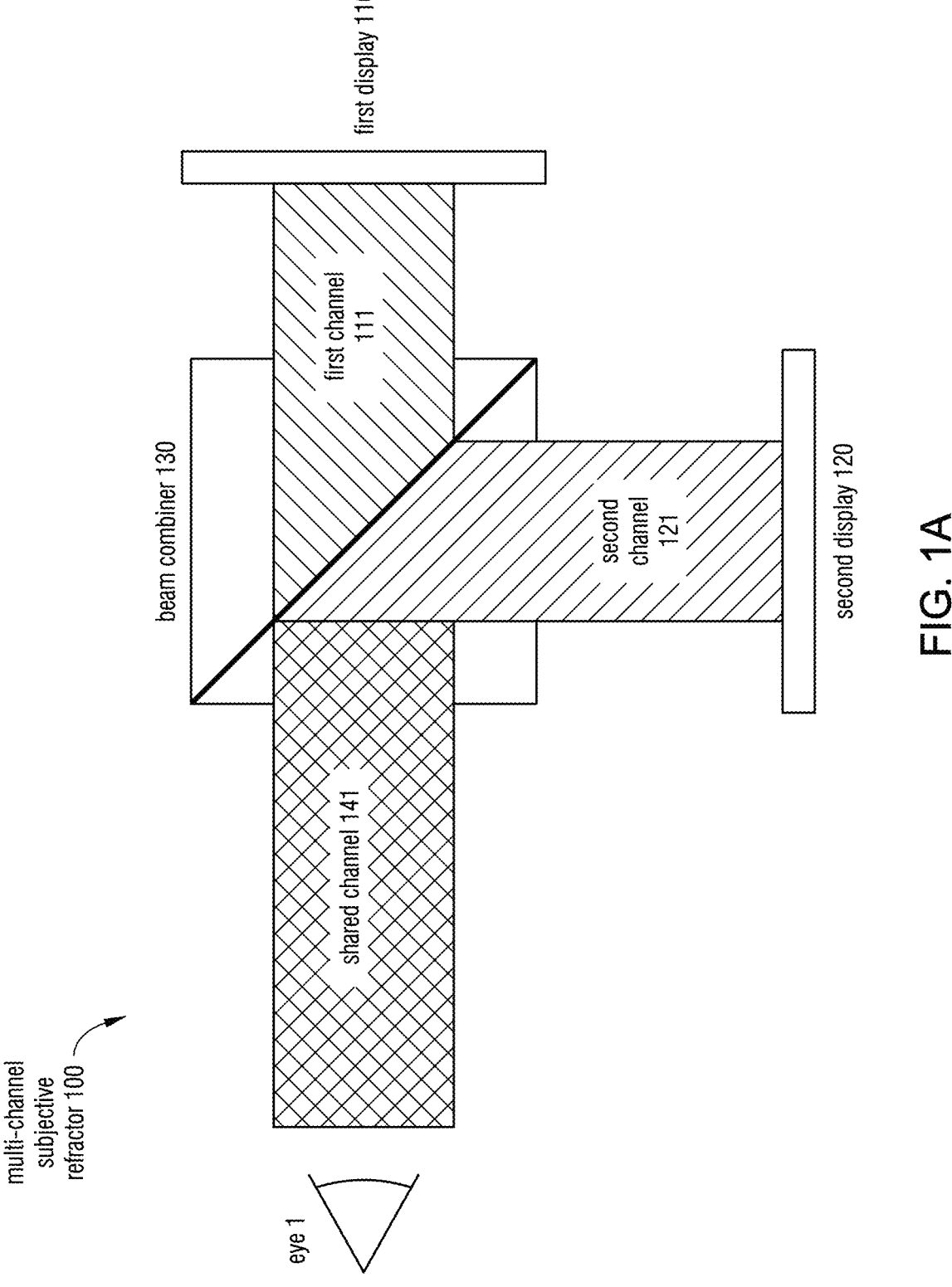
FIGS. 1A-B show schematics of a multi-channel subjective refractor.
Figure 1B:
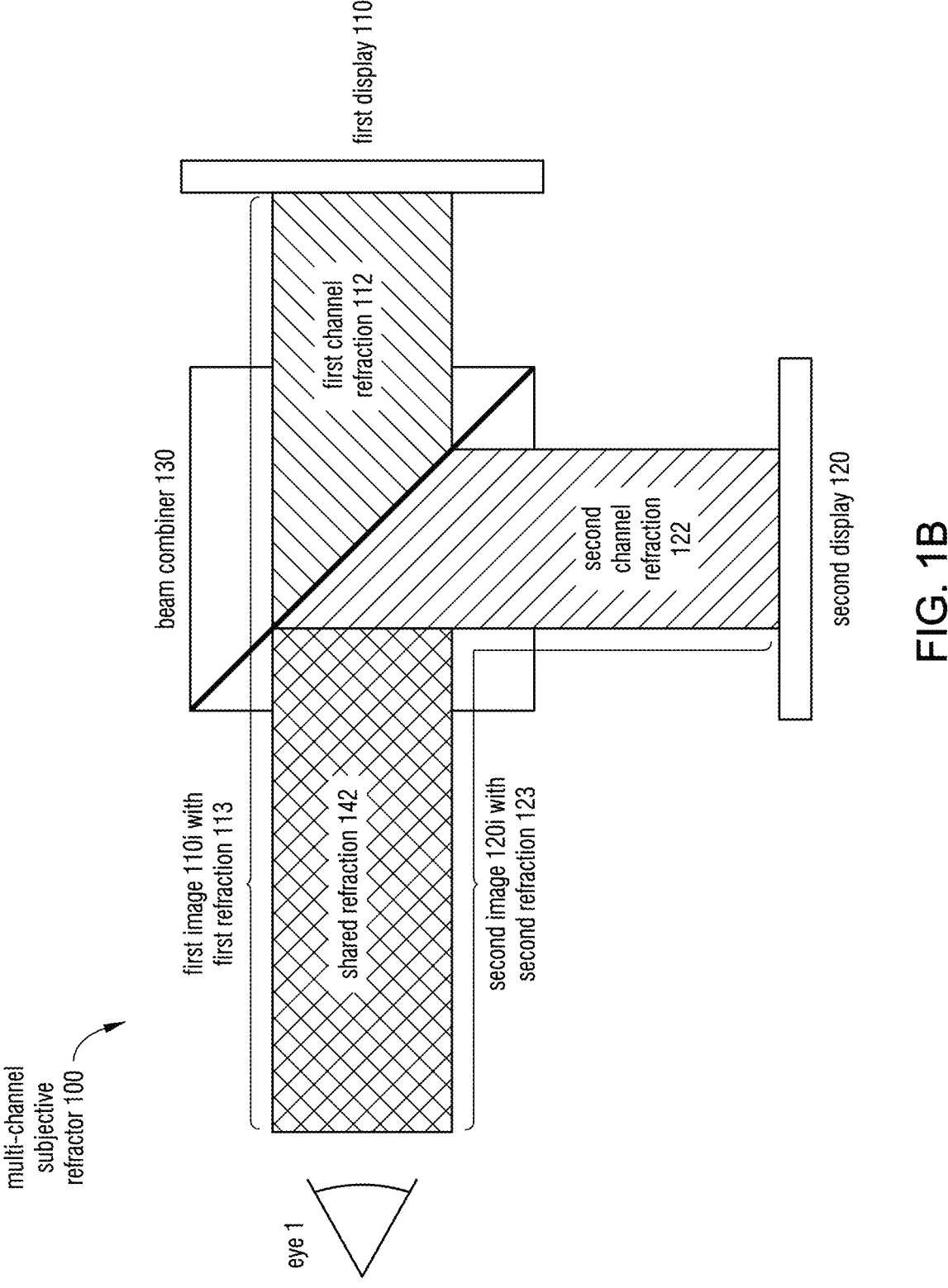

FIGS. 1A-B show that the above-described needs can be addressed by a multi-channel subjective refractor 100 that includes a first display 110 to generate a first image 110i; a second display 120 to generate a second image 120i; a first channel 111 to refract the first image 110i with a first channel refraction 112; a second channel 121 to refract the second image 120i with a second channel refraction 122; a beam combiner 130 to receive and to combine the first image 110i and the second image 120i; and a shared channel 141, to receive the first image 110i and the second image 120i from the beam combiner 130; to refract, in combination with the first channel 111, the first image 110i with a first refraction 113; to refract, in combination with the second channel 121, the second image 120i with a second refraction 123; and to present the first image 110i with the first refraction 113 and the second image 120i with the second refraction 123 to an eye 1 simultaneously.

In operation, the patient is prompted to choose which of the simultaneously presented first image 110i with the first refraction 113 or the second image 120i with the second refraction 123 appears sharper. As discussed in relation to FIGS. 4A-B, following practical reasons and historical practices, often the first image 110i and the second image 120i are the same letters of an eye chart, and only their refractions 113 and 123 are different. This prompting for a choice between two, simultaneously presented images is repeated iteratively to scan the relevant refraction space. Which refraction is chosen as the sharpest by the patient can then be used by the optometrist to prescribe a spectacle lens.

Embodiments of the multi-channel subjective refractor 100 may have a patient-facing front that is similar to wavefront aberrometers. This patient-facing front can be sleeker than traditional refractors.

It is mentioned that the beam combiner 130 is often also called a beam splitter—the two names just reflecting forward and backward operation of the same prismatic structure, with its diagonal surface covered with partially reflecting coating. In some embodiments of the multi-channel subjective refractor 100, the first channel 111 and the second channel 121 can share an optical aperture, or axis, after being combined by the beam combiner 130. In some cases, they can also share an aperture.

Refraction is a broad category, relating to various wavefront modification of the generated first and second images 110i and 120i. In particular, in some embodiments of the multi-channel subjective refractor 100, the first channel refraction 112 comprises at least one of a first channel defocus and a first channel cylinder; the second channel refraction 112 comprises at least one of a second channel defocus and a second channel cylinder; the first refraction 113 comprises at least one of a first defocus and a first cylinder; and the second refraction 123 comprises at least one of a second defocus and a second cylinder. Broader definitions of refraction could also include higher order wavefront modifications. For completeness, while defocus is technically a measure of how far a detector plane is from the plane in which image points come into focus, it is closely related to optical power, sphere power, or simply sphere, all having diopters as their units. Defocus expressed as a power can be considered to be the amplitude of the negative of the defocus wavefront aberration which, if added to the system, would cause the image to land on the detector plane. The cylinder power, or astigmatism, can be considered the difference in defocus values required to get the system to focus along two orthogonal directions (axes) at the image plane. The cylinder also has an angular orientation, and thus is best represented by a vector that has both magnitude and direction. In general, the two main axes 1 and 2 are the main axes of curvature of the lens, and are 90° apart. The direction of the main axes, for practical purposes, can be the x and y axes, or two axes that are rotated by 45 degrees.

Figure 2A:
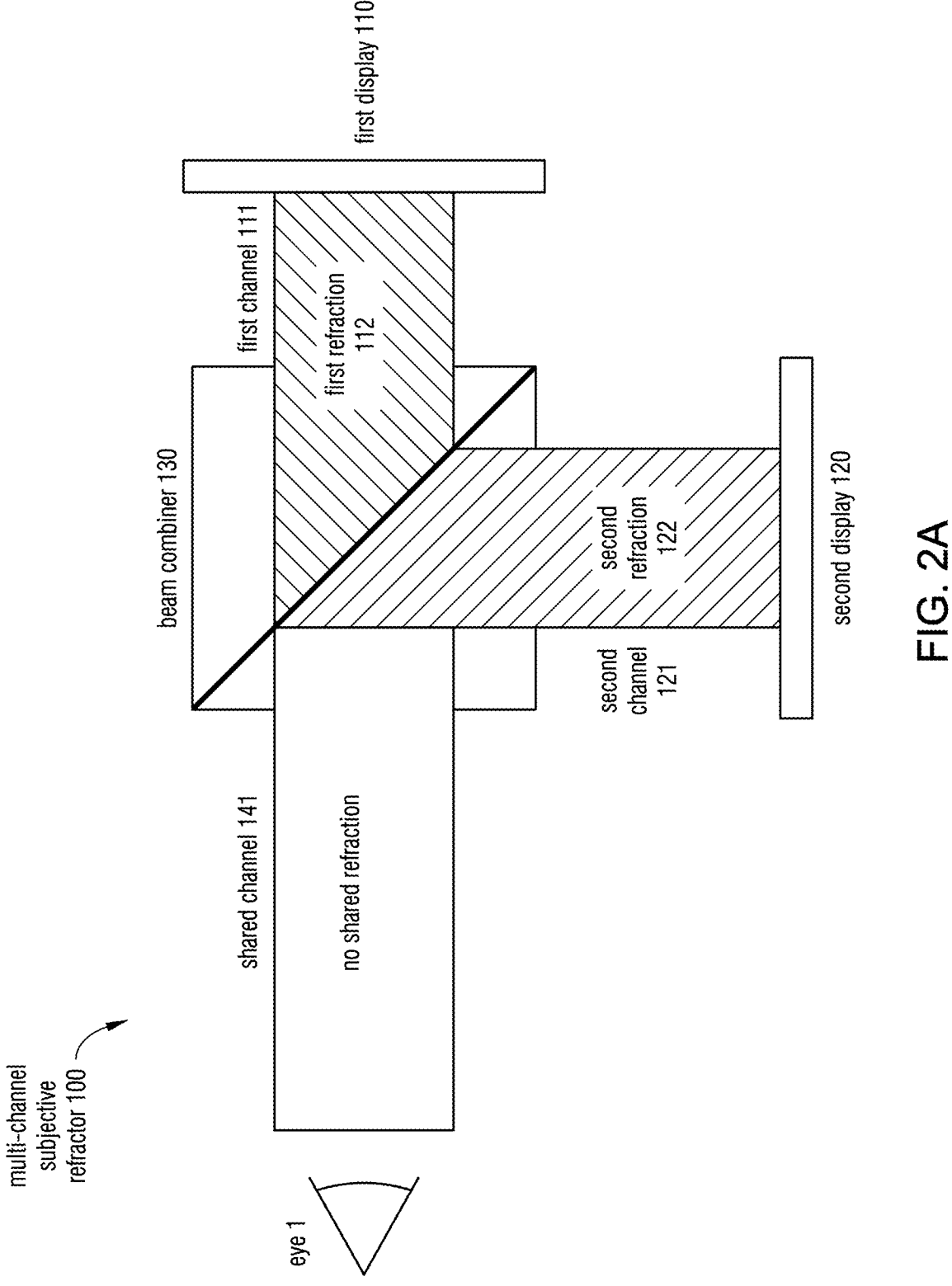
FIGS. 2A-B show embodiments of the multi-channel subjective refractor with no shared refraction in the shared channel.
Figure 2B:
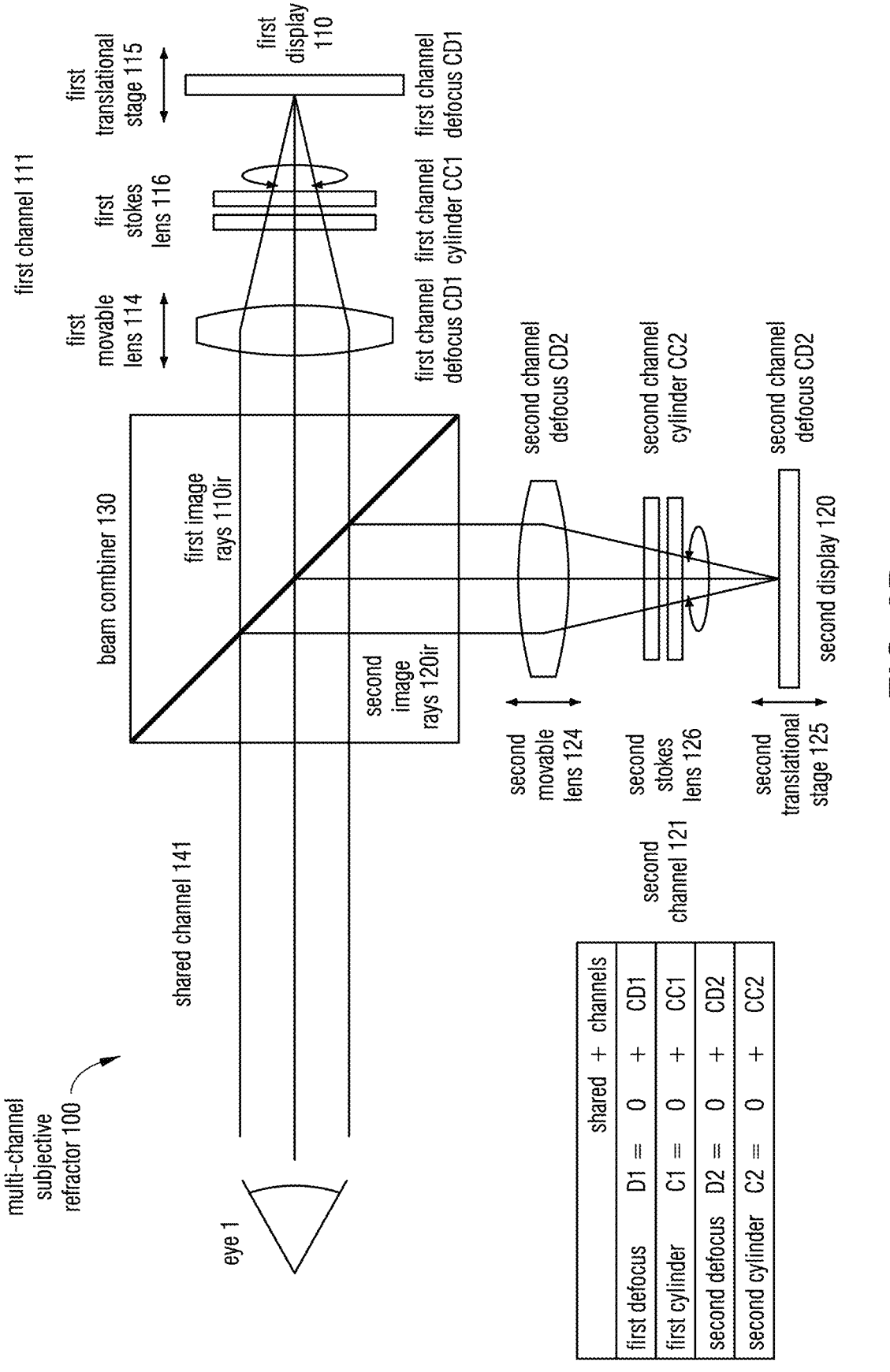

The scope of the above used "refractive combination" of the first and second channels 111/121 with the shared channel 141 is broad. In some embodiments, it may not even have any refractive contribution from the shared channel 141 itself. FIGS. 2A-B show such an embodiment of the multi-channel subjective refractor 100, where the shared channel 141 is not configured to refract the first image 110i and the second image 120i at all. In these embodiments, the first channel 111 provides the entire first refraction 113 for the first image 110i, and the second channel 121 provides the entire second refraction 123 for the second image 120i. In other words, in these embodiments the first channel refraction 112 equals the entire first refraction 113, the second channel refraction 122 equals the entire second refraction 123, and the refractive combination with the shared channel 141 receives no contribution from the shared channel 141.

FIG. 2B shows in a bit more detail that the first channel 111 can be configured to refract the first image 110i with the first defocus D1 and the first cylinder C1; and the second channel 121 can be configured to refract the second image 120i with the second defocus D2 and the second cylinder C2. As said above, in these embodiments, the first defocus D1 equals a first channel defocus CD1, the first cylinder C1 equals a first channel cylinder CC1; the second defocus D2 equals a second channel defocus CD2, and the second cylinder C2 equals a second channel cylinder CC2. In these embodiments, the first channel 111 may comprise at least one of a first movable lens 114, a first variable power lens, a first deformable mirror, a first phase modulator, and a first translational stage 115 to move the first display 110, to refract the first image 110i with the first defocus D1; and a first stokes lens 116, to refract the first image 110i with the first cylinder C1; and the second channel 120 may comprise at least one of a second movable lens 124, a second variable power lens, a second deformable mirror, a second phase modulator, and a second translational stage 125 to move the second display 120, to refract the second image 110i with the second defocus D2; and a second stokes lens 126, to refract the second image 120i with the second cylinder C2. Only some of the listed optical elements are shown in FIG. 2B.

The just-listed refractive combinations are summarized in the inserted table in FIG. 2B. Since the shared channel 141 is not configured to contribute any refraction, all four types of the refractions are generated solely by the first and second channel 111/121:

| | shared + channels |
|---|---|
| first defocus | D1 = 0 + CD1 |
| first cylinder | C1 = 0 + CC1 |
| second defocus | D2 = 0 + CD2 |
| second cylinder | C2 = 0 + CC2 |

For future reference, the shared defocus optionally caused by the shared channel 141 will be referenced as SD, and the optional shared cylinder as SC. From here on these abbreviations, or labels, will be used for such comprehensive refraction tables that characterize the various embodiments.

The "Stokes pair" or simply "Stokes lens" refers to a pair of cylindrical lenses of equal and opposite cylindrical power that can be rotated relative to each other about their shared optical axis. Their azimuthal positions can create a cylinder, or astigmatism, with a magnitude within a range, and with the cylinder direction pointing to any desired cylinder angle, by the suitable rotation of the two cylindrical lenses.

The above-described refractions can be described and determined by ray tracing, or following rays emitted by representative points of the first and second displays 110/120, such as the shown first image rays 110$ir$ and second image rays 120$ir$. It is worth noting that in the shown embodiment, the first image rays 110$ir$ and the second image rays 120$ir$ are approaching the eye 1 in a nominally collimated manner, in order to make the multi-channel subjective refractor 100 project the displayed images as distant objects. In addition, optical rays propagating from the displays 110/120 are preferably telecentric, so that the apparent size of the projected images doesn't change as the images are defocused.

FIGS. 3A-F show several embodiments of the multi-channel subjective refractor 100 where the shared channel 141 is configured to refract the first image 110$i$ and the second image 120$i$ with a shared refraction 143 that includes at least one of a shared defocus SD and a shared cylinder SC. As shown in FIGS. 3B-F, in these embodiments, the shared channel 141 may include at least one of a shared movable lens 144, a shared variable power lens, a shared deformable mirror, or a shared phase modulator, to refract the first image 110$i$ and the second image 120$i$ with the shared defocus SD; and a shared Stokes lens, deformable mirror, or phase modulator 146, to refract the first image 110$i$ and the second image 120$i$ with the shared cylinder SC. In some of these multi-channel subjective refractors 100, the first channel 111 may include at least one of a first movable lens 114, a first variable power lens, a first deformable mirror, a first phase modulator, or a first translational stage 115 to move the first display 110, to refract the first image 110$i$ with the first channel defocus CD1 that combines with the shared defocus SD to create the first defocus D1; and a first stokes lens 116, to refract the first image 110$i$ with the first channel cylinder CC1 that combines with the shared cylinder SC to create the first cylinder C1; or the second channel 121 may include at least one of a second movable lens 124, a second variable power lens, a second deformable mirror, a second phase modulator, or a second translational stage 125 to move the second display 120, to refract the second image 120$i$ with the second channel defocus CD2 that combines with the shared defocus SD to create the second defocus D2; and a second stokes lens 126, to refract the second image 120$i$ with the second channel cylinder CC2 that combines with the shared cylinder SC to create the second cylinder C2. Accordingly, a generic summary of these refractive contributions can be summarized in this refraction table:

|  | shared + channels |
| --- | --- |
| first defocus | D1 = SD + CD1 |
| first cylinder | C1 = SC + CC1 |
| second defocus | D2 = SD + CD2 |
| second cylinder | C2 = SC + CC2 |

In the embodiments of FIGS. 2A-B, the shared channel 141 did not contribute any refraction SD or SC to the "combined refractions". Somewhat analogously, in the embodiments of FIGS. 3A-F, one of the first channel 111 or second channel 121 may not be configured to refract the corresponding first image 110$i$ or second image 120$i$ at all, and thus may not contribute to the combined refractions. In those cases, the shared refractions will produce the entirety of the first or second refractions, whichever has no channel refraction.

Here, a general note on the design. The human eye of patients can exhibit refractive deficiencies from −20 diopters to +20 diopters in defocus, in some extreme cases even more. Therefore, refractors also have to be able to cover such very wide ranges of diopters to provide comprehensive utility for the optometrists. However, covering such a wide power range requires a movable lens with a long moving stage, or a wide collection of lenses, to be inserted into the optical path with corresponding mechanics, or a variable power lens with a wide range of power variation, or a movable stage with long rails to move the display. Each of these engineering solutions takes up a lot of space, requires a number of moving parts, and increases the cost. In the "no shared refraction 143" multi-channel subjective refractors 100 of FIGS. 2A-B, both the first channel 111 and the second channel 121 have to be able to cover such a wide range of refractions with corresponding expensive and expansive optical designs. This makes the size of these refractors 100 big and the price high. In contrast, in the multi-channel subjective refractors 100 of FIGS. 3A-F which have a shared refraction 143, only the shared channel 141 needs to cover the wide range of refractions, and the first channel 111 and second channel 121 only need to cover a narrow differential refraction which is the narrow refraction difference between the first refraction 113 and the second refraction 123, presented to the patient as the comparison steps or intervals. This refraction can vary in a much narrower range, such as a defocus range of −1 D to +1 D. Therefore, in such shared refraction embodiments of the multi-channel subjective refractor 100, only the optical elements in the shared channel 141 cover the wide range of sphere and cylinder powers, and are therefore expansive and expensive, while the small and narrow-range optical elements in the first channel 111 and second channel 121 cover only the much-narrower differential refraction range, and are therefore small and much less expensive. Such shared refraction embodiments therefore offer benefits for an optometry practice.

In an example, the shared channel 141 can be configured to cover a wide defocus range of −20 D to +20 D, while both the first channel 111 and the second channel 121 can be configured to cover only the narrow differential defocus range of −1 D to +1 D. In another example, the shared channel 141 can be configured to cover the wide defocus range of −20 D to +20 D, the wide cylinder power range of −10, or −15, cylinder D to +10, or +15, cylinder D, and the wide cylinder angle range from 0 to 180 degrees, whereas the first channel 111 and the second channel 121 can be configured to cover only the differential defocus range of −1.5 D to +1.5 D and the differential cylinder power range of −1 cylinder D to +1 cylinder D. Similarly, in some embodiments of the multi-channel subjective refractor 100 at least one of the first channel defocus CD1, the first channel cylinder CC1, the second channel defocus CD2 and the second channel cylinder CC2 are all less than two diopters, where "diopter" refers inclusively to both sphere and cylinder diopters.

Of course, in some embodiments of the multi-channel subjective refractor 100, at least one of the first channel 111 and the second channel 121 can cover wide diopter ranges. For example, at least one of the first channel defocus CD1 and the second channel defocus CD2 can cover a range of +/−15 D, in some cases +/−20 D and at least one of the first channel cylinder CC1 and the second channel cylinder CC2 can cover +/−10 D, in some cases +/−15 D.

A further simplification can be achieved in some embodiments of the multi-channel subjective refractor 100 by using a design where one of the first channel 111 or the second channel 121 is not configured to refract the corresponding first image 110*i* or second image 120*i* at all. In such embodiments, one of the first refraction 113 or the second refraction 123 simply equals the shared refraction 143, and the differential refraction is generated only by the other, refracting channel. Finally, in some embodiments, different portions of the differential refraction can be implemented in different channels. For example, the differential defocus can be implemented only in the first channel 111 as CD1, but not accompanied by a differential channel cylinder (i.e. CC1=0), while the differential cylinder is implemented in the second channel 121 as CC2, wherein the second channel 121 does not have any defocus: CD2=0.

Figure 3A:
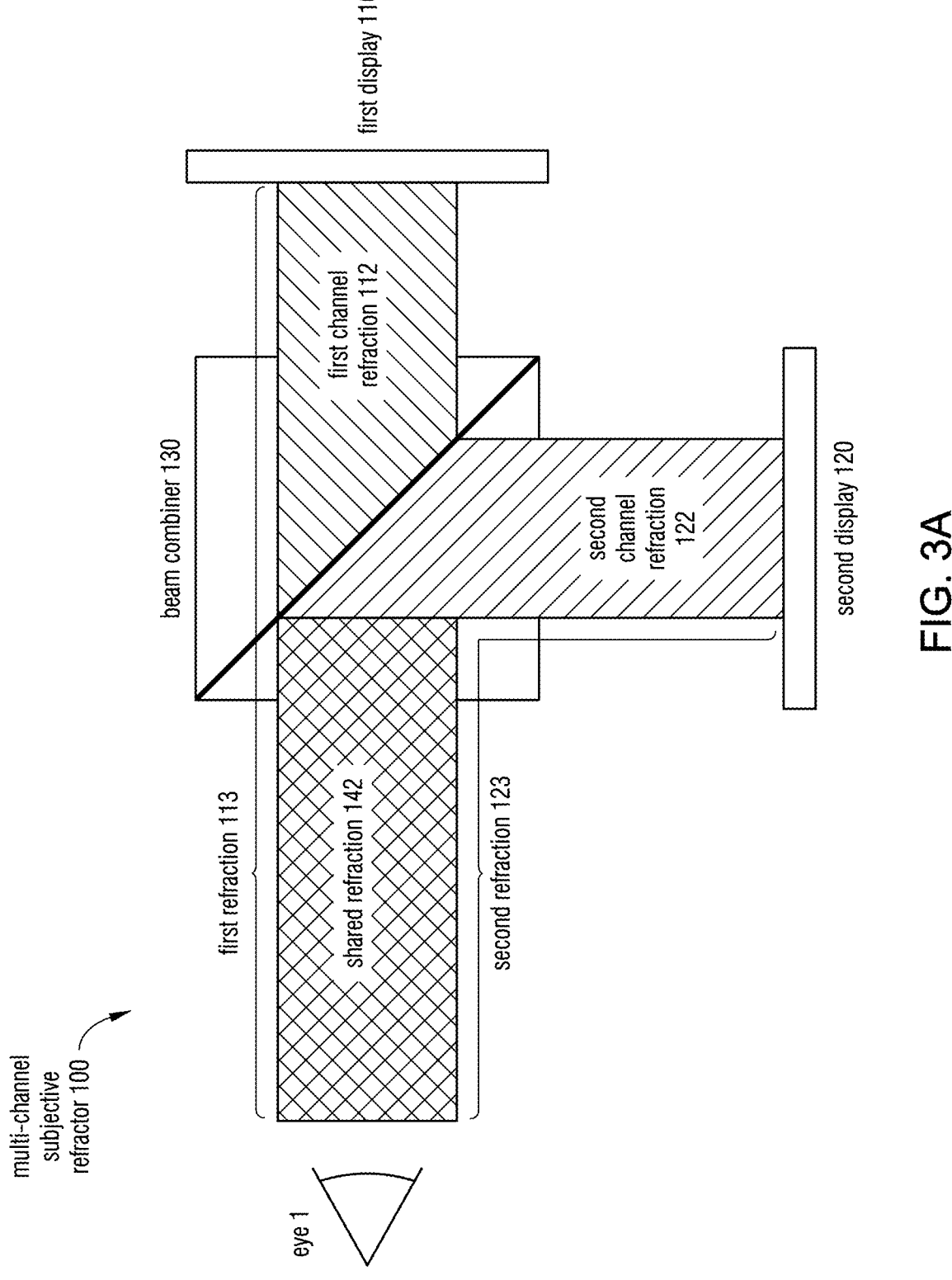
FIGS. 3A-F show embodiments of the multi-channel subjective refractor with refraction in the first, second and shared channels.
Figure 3B:
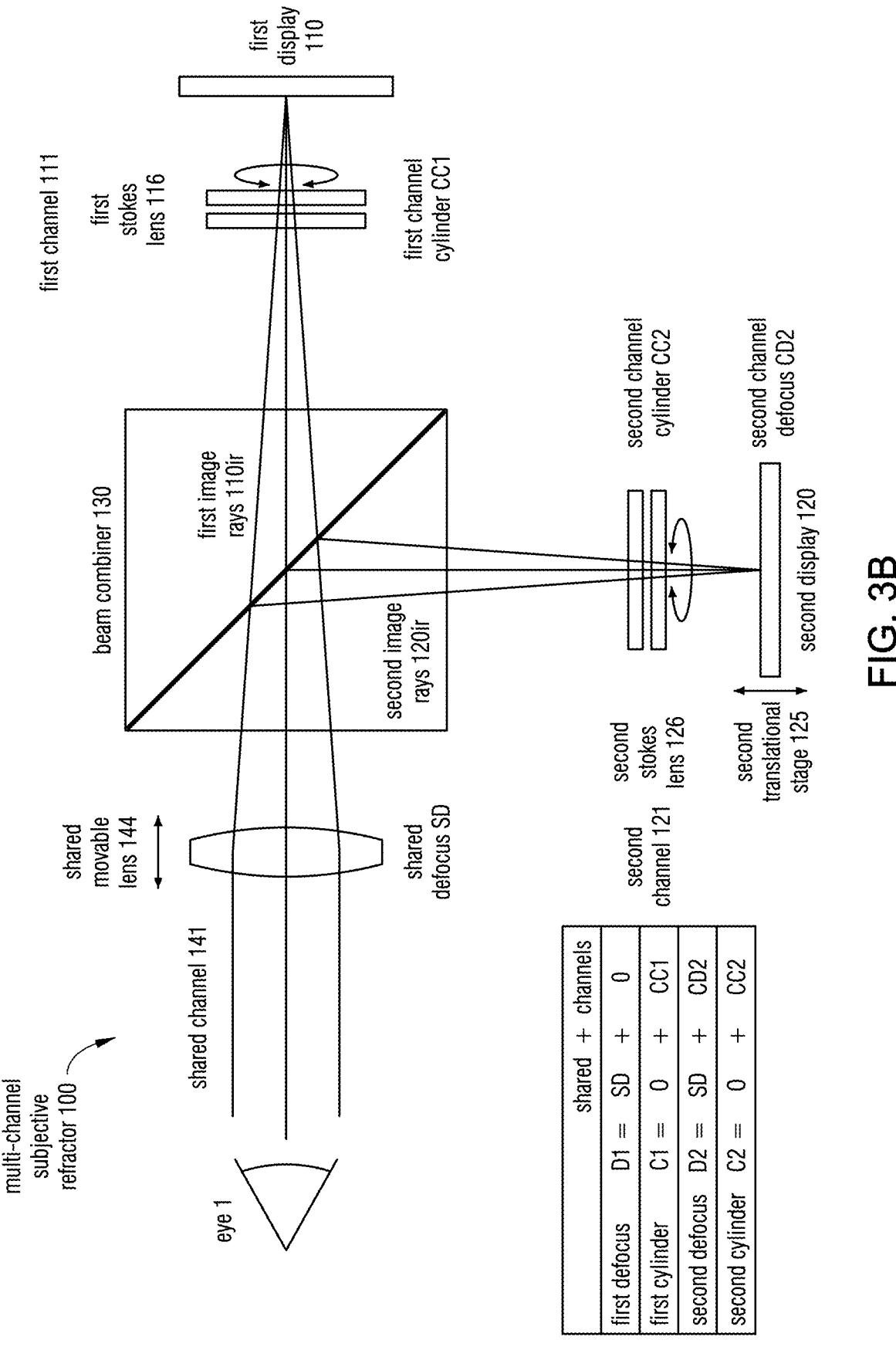

FIGS. 3B-F show several embodiments of such "shared-refraction plus distributed differential refraction" designs. In particular, FIG. 3B shows an embodiment where the first channel 111 is only refracts the first image 110*i* with a first channel cylinder CC1 via a first stokes lens 116, while the second channel 121 is configured to refract the second image 120*i* with a second channel defocus CD2 via a second translational stage 125 that moves the second display 120 along the axis. In some cases, the second channel 121 can further include a second stokes lens 126 to also refract the second image with a second channel cylinder CC2, as shown. In this embodiment, the shared channel 141 includes a shared movable lens 144 to refract both images with a shared defocus SD, but not with a shared cylinder SC. The summary refraction table reads as:

| | shared + channels |
|---|---|
| first defocus | D1 = SD + 0 |
| first cylinder | C1 = 0 + CC1 |
| second defocus | D2 = SD + CD2 |
| second cylinder | C2 = 0 + CC2 |

Figure 3C:
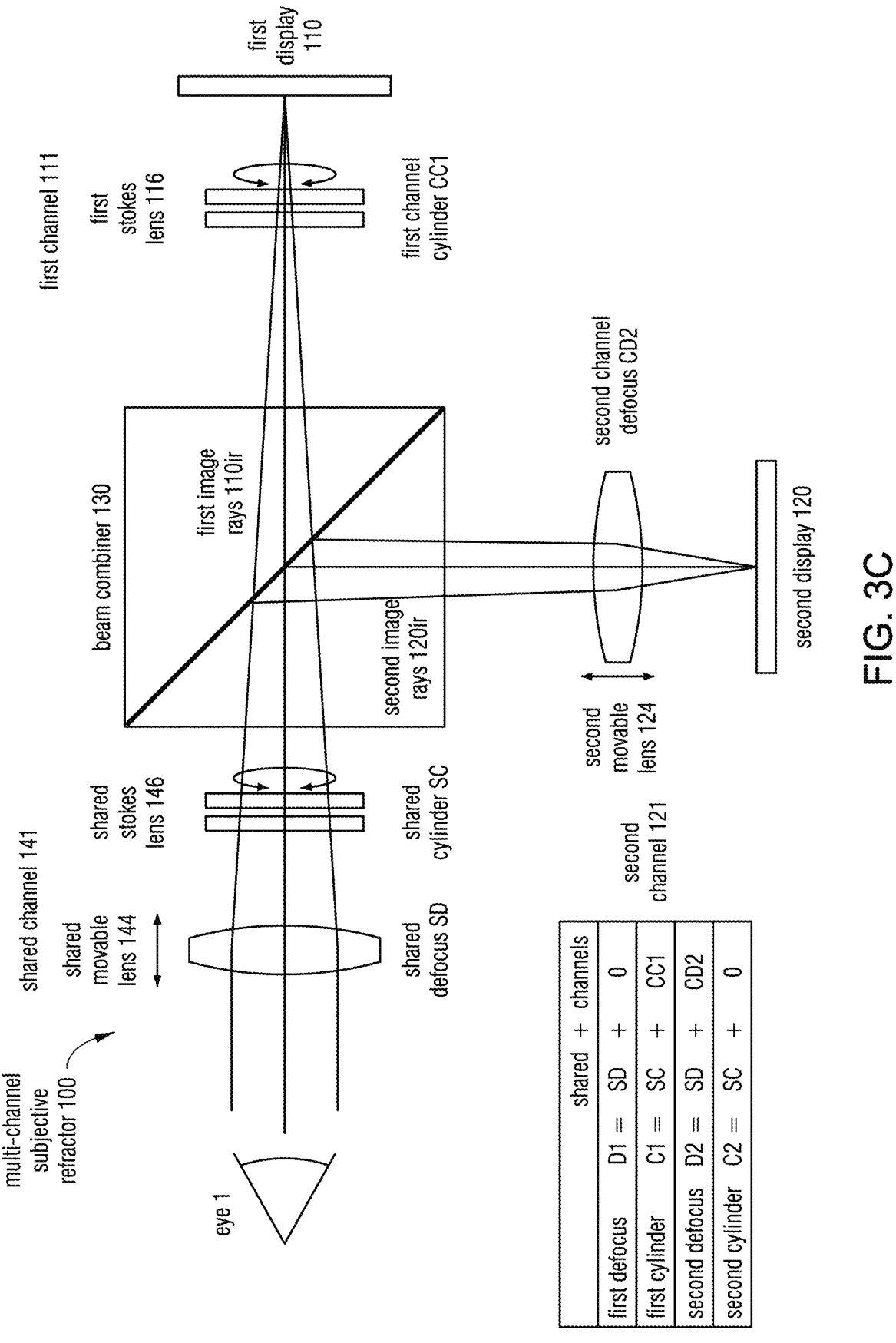

FIG. 3C shows another exemplary embodiment of the multi-channel subjective refractor 100, where the shared channel 141 includes both the shared movable lens 144 to refract the first and second images 110*i*/120*i* with the shared defocus SD, and a shared stokes lens 146 to refract the first and second images 110*i*/120*i* with a shared cylinder SC. In addition, the first channel 111 has the first stokes lens 116 to refract the first image 110*i* with the first channel cylinder CC1, and the second channel 121 has a second movable lens 124 to refract the second image 120*i* with the second channel defocus CD2. The corresponding refraction table reads as:

| | shared + channels |
|---|---|
| first defocus | D1 = SD + 0 |
| first cylinder | C1 = SC + CC1 |
| second defocus | D2 = SD + CD2 |
| second cylinder | C2 = SC + 0 |

Figure 3D:
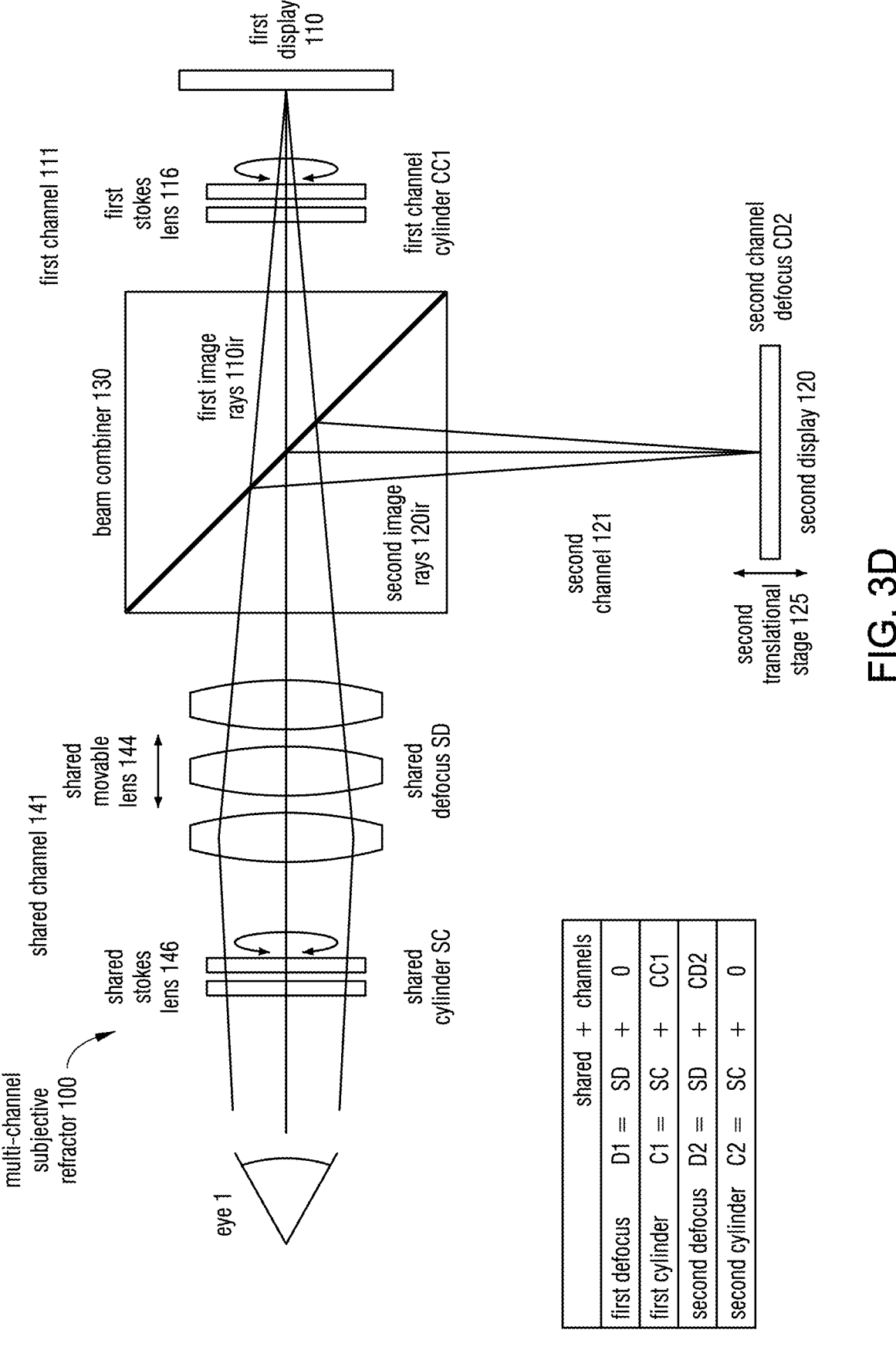

FIG. 3D shows yet another implementation of the multi-channel subjective refractor 100. Here the shared channel 141 again includes the shared movable lens 144 to refract the first and second images 110*i*/120*i* with the shared defocus SD, and also includes the shared stokes lens 146 to refract the first and second images 110*i*/120*i* with a shared cylinder SC. The first channel 111 has the first stokes lens 116 to refract the first image 110*i* with the first channel cylinder CC1, and the second channel has the second translational stage 125 to translate the second display 120 to refract the second image 120*i* with the second channel defocus CD2. FIG. 3D shows that in this description the term "lens" is used in a broad, inclusive way to refer to any lens assembly that satisfies the overall function of a lens. Lens assemblies are often used in place of individual lenses to optimize the system performance in face of other challenges. These include, for example, the need to reduce chromatic aberration by using a crown-flint doublet in place of a single lens as the shared movable lens 144, as shown in FIG. 3D. These lens assemblies are also referred to as achromats, or as cemented doublets. Other lens assemblies may be used to increase contrast sensitivity or to reduce thermal expansion coefficients. The refraction table once again reads:

| | shared + channels |
|---|---|
| first defocus | D1 = SD + 0 |
| first cylinder | C1 = SC + CC1 |
| second defocus | D2 = SD + CD2 |
| second cylinder | C2 = SC + 0 |

Figure 3E:
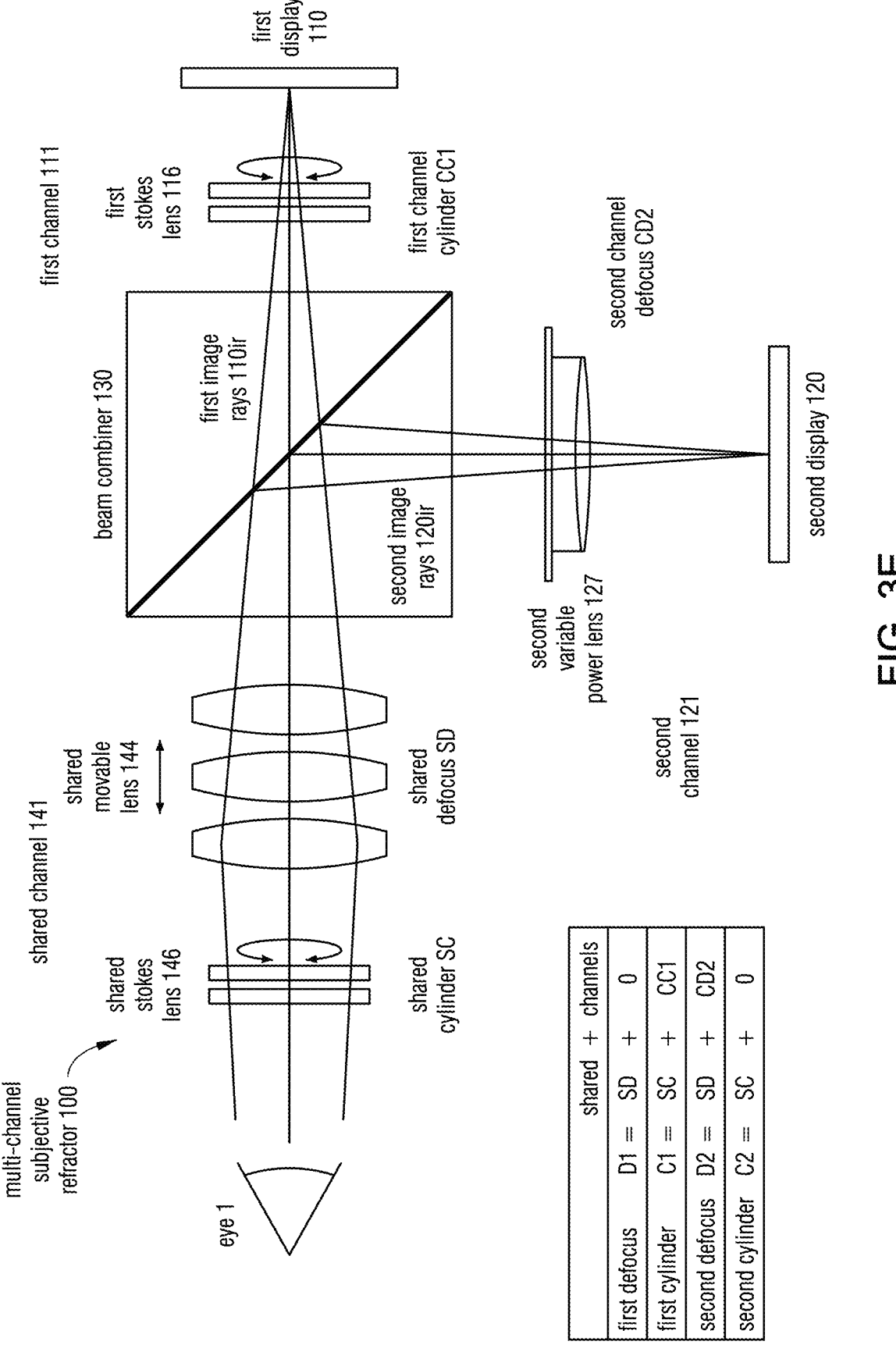

FIG. 3E shows yet another embodiment of the multi-channel subjective refractor 100. The main difference relative to FIG. 3D is that in the second channel 121, the second channel defocus CD2 is generated by a second variable power lens 127, instead of the second movable lens 124, or the second translational stage 125 for the second display 120. There is a wide and growing selection of innovative variable power lenses 127. These include fluid filled lenses, where the curvature and therefore the power of the lens is varied by controlling the amount and possibly the spatial distribution of the fluid by applying pressure, or pumping fluids from fluid reservoirs. Variable power lenses 127 can also be formed with suitably engineered and spatially distributed liquid crystals where the focus is varied with applying an external voltage. Yet other solutions may also be used, like Alvarez lenses, where two optical elements with a cubic or more complex profile are rotated relative to each other. Some embodiments may achieve the effect of variable power by using a deformable mirror. The refraction table of FIG. 3E is the same as for FIG. 3D, as shown.

Figure 3F:
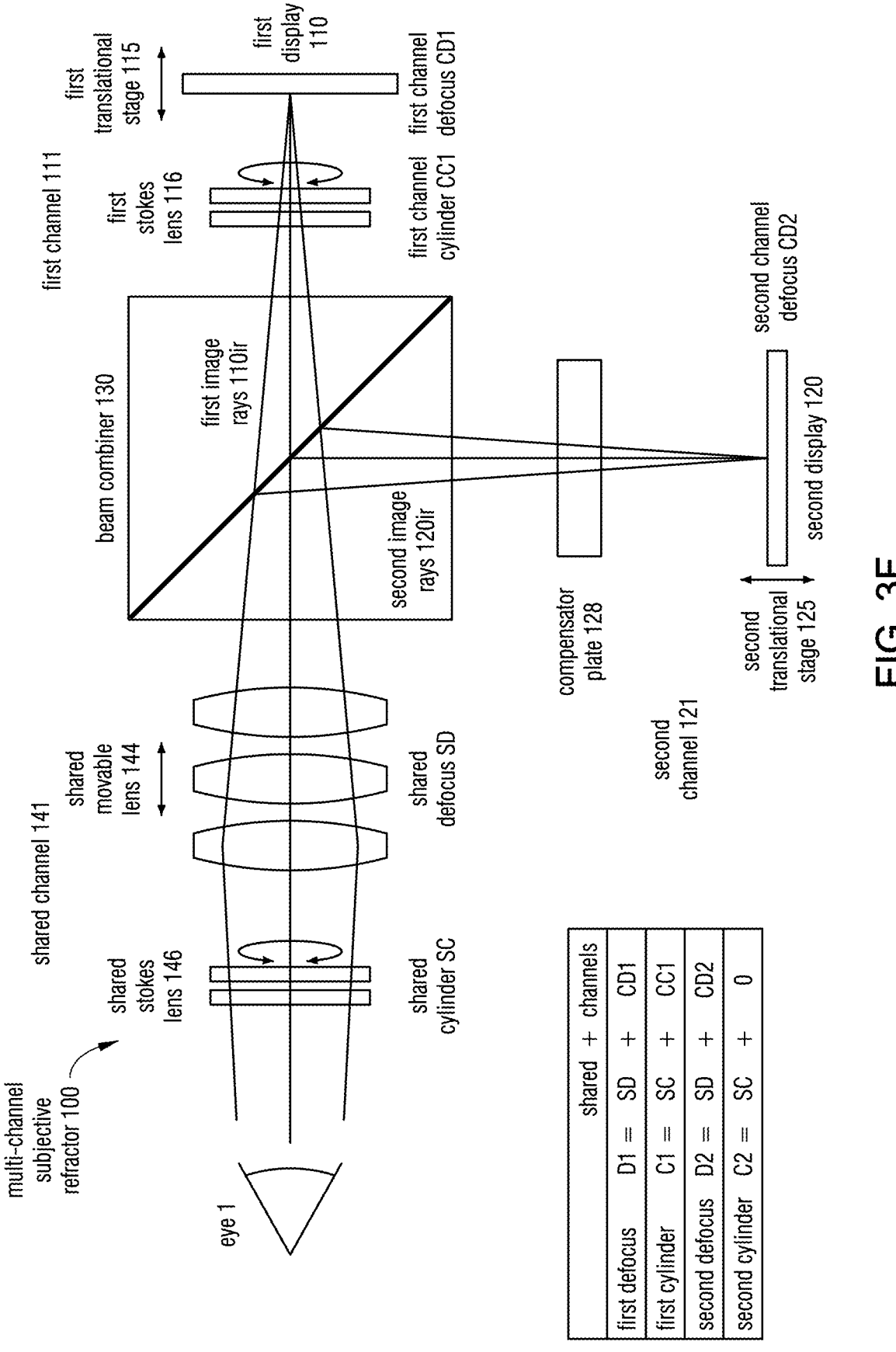

Finally, FIG. 3F shows yet another embodiment of the multi-channel subjective refractor 100. This again has the shared movable lens (assembly) 144 to refract the first and second images 110*i*/120*i* with a shared defocus SD, and the shared stokes lens 146 to refract the images with a shared cylinder SC. The first channel 111 includes a first translational stage 115 to translate the first display 110 to refract the first image 110*i* with the first channel defocus CD1, and the first stokes lens 116 to refract the first image 110*i* with the first channel cylinder CC1. The second channel 121 includes the second translational stage 125 to translate the second display 120 to refract the second image 120*i* with the second channel defocus CD2. In addition, this embodiment may include a compensator plate 128 that can be included to compensate higher order aberrations or chromatic aberrations that emerge between the first image 110*i* and the second image 120*i* because they propagate through different optical elements. This embodiment includes translational stage 115 and 125 in both channels, and thus contains more degrees of freedom than minimally required. Such redundant elements in this and in earlier-described embodiments may be included to provide added control and to further minimize unwanted optical effects, such as chromatic aberrations or higher order aberrations. The refraction table for the embodiment of FIG. 3F reads as:

|  | shared + channels |
| --- | --- |
| first defocus | D1 = SD + CD1 |
| first cylinder | C1 = SC + CC1 |
| second defocus | D2 = SD + CD2 |
| second cylinder | C2 = SC + 0 |

The above-described large number of embodiments of the multi-channel subjective refractor 100 are examples of configuring the first channel 111, the second channel 121 and the shared channel 141 to enable an independent adjustment of the first refraction 113 and the second refraction 123. Before moving on, it is also mentioned that embodiments of the multi-channel subjective refractor 100 can be collimating, as the multi-channel subjective refractor 100 can image the displays 110/120 to infinity. Typically, this effect is achieved by emitting a collimated beam through an exit pupil towards the eye 1 of the patient, as shown with the tracing of the first and second image rays 110*ir* and 120*ir*. Further, in some simple optical designs, the projected size of the objects may change as the focus is changed. However, this can lead to an error in the patient's perception as a larger image is often perceived as "clearer" by a patient. Some embodiments of the multi-channel subjective refractor 100 preempt this problem by making use of an optics (first channel 111, second channel 121 and shared channel 141) that is telecentric, and thus the apparent size of the projected object (images 110*i*/120*i*) does not change with a changing of the focus. Other embodiments do not need such a telecentric optic, as the size of the images 110*i*/120*i* can be also changed electronically on the displays 110/120.

It is mentioned that recently a new class of intraocular lenses has been introduced that are light adjustable non-invasively after implantation. For these light adjustable lenses (LALs), the optometrist performs a refraction measurement after the implantation to measure the difference of the refraction of the implanted LAL from the planned, or patient-preferred refraction. These differences are typically small, typically in the 0.5 D-1.5 D range. Therefore, some embodiments of the multi-channel subjective refractor 100 that are intended to be used only in conjunction of the LAL adjustment procedure, can be made much smaller, since the movable lenses 114/124/144 and the translational stages 115/125 need to cover only the limited range of optical refractive powers of about −2 D to +2 D, instead of the general purpose refractors that typically cover much wider ranges up to −20 D to +20 D. Smaller multi-channel subjective refractors 100 with limited measurement and adjustment ranges naturally cost less, and thus can bring the medical benefits of the LAL to a wider range of patients.

For completeness it is mentioned that in embodiments where the covered diopter range is wider, additional optical design elements may need to be introduced. For example, if the first channel 111, the second channel 121, or the shared channel 141 is designed to cover a wide diopter range of −10 D/+10 D, then the beam may need to be deflected out by a mirror toward a Porro prism, from where the returning beam is reflected back into the channel by a second mirror. In some designs, the Porro prism can provide coverage for the −10 D/+10 D diopter range by being moved by 3-5 inches on a moving stage.

Figures 4A, 4B:
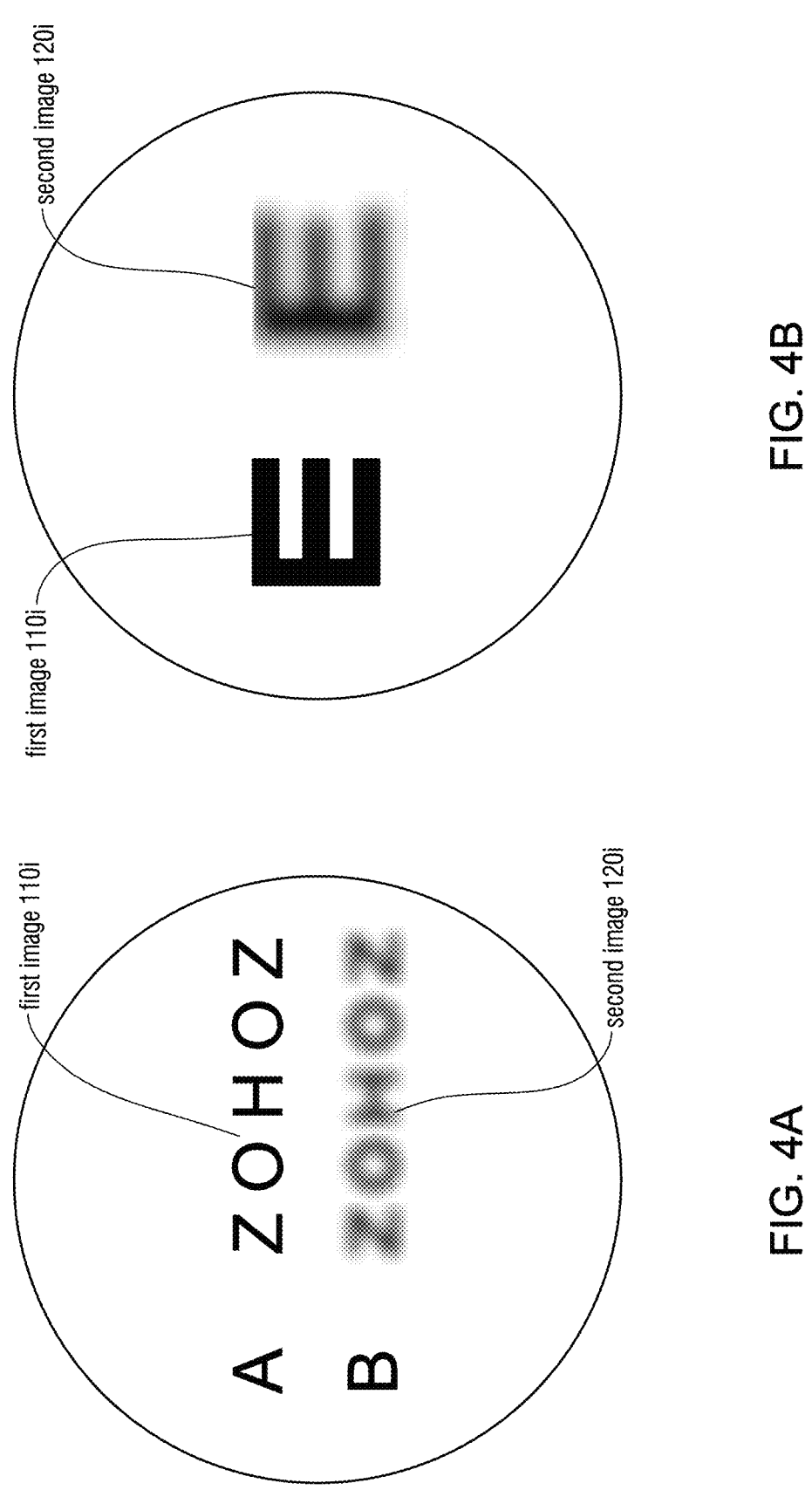
FIGS. 4A-B show two images with different refractions.

FIGS. 4A-B show that embodiments of the multi-channel subjective refractor 100 can be configured to present the first image 110*i* with the first refraction 113 and the second image 120*i* with the second refraction 123 simultaneously as an up-down image pair (FIG. 4A), or a side-by-side image pair (FIG. 4B), or any other positioning of an image pair. Corresponding to these presentation types, multi-channel subjective refractors 100 can also be called dual field refractors, simultaneous refractors, parallel refractors, or side-by-side refractors. The presented images can be of a wide variety, including actual photos and pictures, or a line of a Snellen chart, or individual letters, for example the often used capital E, or any kind of eye chart, or a log MAR chart, or an armed force target. The patient's communication may be made clearer by attaching a label to the first image 110*i* and the second image 120*i*, e.g. the letters A and B in FIG. 4A.

While the electronics of the multi-channel display 100 clearly enables the first display 110 and the second display 120 to generate different first and second images 110*i* and 120*i*, the patient may find comparing identical images with different refractions easier. Also, showing the same line of an eyechart only with different refractions for comparison is the practice optometrists have been following historically. Therefore, in many embodiments of the multi-channel subjective refractor 100 the first image 110*i* and the second image 120*i* may be the same, and can include one or more letters of an eye chart, of a Snellen chart, of an army target, or any other figure of an examination chart, which is not necessarily alphanumerical.

FIGS. 4A-B show clearly a key aspect of the multi-channel subjective refractor 100: that the patient is presented simultaneously, in parallel, with the images to be compared. The images are separated not in time, but only in space. As discussed, such refractors 100 (1) eliminate the mental, cognitive pressure on the patient to keep the memory of the visual clarity of previous images active; (2) enable a more accurate comparison because the two images are presented simultaneously and can be directly compared; (3) eliminate the frustrating repeated "back and forth" requests by patients to the optometrist/OD; and (4) greatly reduce the chair time, or time in the lane, because the comparison proceeds much faster, thereby substantially improving the workflow and economy of the optometrist office.

The process of exploring the relevant refraction space can be further accelerated by designing multi-channel subjective refractors 100 that include one or more additional channels, configured to present one or more additional images (beyond the first and second images 110*i*/120*i*) with corresponding refractions simultaneously for the eye. Such multi-channel subjective refractors 100 can thus present three, four, or more images simultaneously for the patient, who is then prompted to choose the sharpest image from the three, four or more images.

Here we make some comparative remarks. As known, the human eye refracts light with different wavelengths with slightly different indices of refraction. This is called dispersion, or chromatic aberration. The changing refractive index causes the optical power to change with wavelength. The difference of the eye's optical power between red and green light is approximately 0.5 D in the human eye. As a consequence, if the red component of an incoming light is focused on the retina, then the green component is focused about 0.2 mm in front of the retina. This fact is used in the so-called duochrome eye tests, when half of the black letters on the optical chart are presented over a red background and half of them over a green background. The effect of the eye's chromatic aberration or dispersion is that if the letters over the red background appear sharp, then the letters over the green background will appear blurry; and vice versa. The underlying theory is that the red and green wavelengths project objects that have an effective difference in refraction of about 0.5 D between them. The red and green colors are approximately symmetric on either side of the yellow color, thought to be key to optimize vision. Therefore, the patient is presented by a sequence of lenses and asked whether the letters over the red or green background appear sharper. The optometrist keeps changing the lenses until equal sharpness is achieved for the letters over the red and green backgrounds, which is taken as a sign that the yellow light is best focused on the retina.

This duochrome test is qualitatively different from the here-described method in several aspects. (1) The duochrome device presents two letters with equal optical power, or refraction, for the eye whereas embodiments of the multi-channel subjective refractor 100 present two letters with different refractions.

(2) In the duochrome test, the apparent difference of refractions is not generated by the device, but by the eye's chromatic aberration only, whereas embodiments of the multi-channel subjective refractor 100 do not rely on the eye's chromatic aberration as they typically present the letters over a white background.

(3) The duochrome test is useless for pseudophakic eyes with implanted diffractive IOLs, because those IOLs has minimal or negligible chromatic aberration. Some non-diffractive IOLs can also have lower chromatic aberration. In contrast, the multi-channel subjective refractor 100 can be very helpfully utilized to refract eyes with IOLs, especially light adjustable IOLs (LALs), where the refraction is an important step of the post-operative lens adjustment.

(4) The goal of the duochrome test is to achieve the patient reporting equally clear vision of the presented two letters, whereas a goal of the multi-channel subjective refractor 100 is the patient reporting one letter being clearer than the other one. Often, it is easier to notice and report a visual difference than to conclude that the visions of two eyes are equally clear.

(5) The duochrome test is not capable of testing and measuring cylinder.

(6) The duochrome method cannot easily change the difference between the two presented refractions unless the wavelengths are changed. The chromatic aberration between 550 nm (green) and 650 nm (red) is approximately 0.5 D. If one wanted to change the power difference, the wavelengths of the projections would have to be changed (for example by changing pigments in the ink or changing the emissive source of an electronic display), which is generally not easy to do with standard materials.

(7) Patients may be confused when presented with objects of two different colors and asked to specify the clearer one. One color may be more pleasant than the other or may appear "brighter" to the patient, influencing the patient's choice. Also, eyes are naturally more sensitive to green wavelengths than red, leading to another potential source of error.

(8) Neural detection and processing differences between green and red signals within the retina and optic nerve may also lead to a source of error in the measurement.

(9) Red-and-green duochrome methods won't work well if the starting state of the refractor is not already close to the patient's prescription. Far away from the ideal refraction, picking the sharper image may be difficult and error-prone for the patient. For this reason, duochrome methods are primarily used only for a potential "final adjustment" of refraction after the refraction has already largely been determined.

Some of these differences are well demonstrated in embodiments of the multi-channel subjective refractor 100, where the first display 110 generates the first image 110i with approximately or precisely the same background color as the second display 120 generates the second image 120i, while the first refraction 113 is different from the second refraction 123.

Yet another distinctive aspect of the multi-channel subjective refractor 100 is that it enables evaluating and optimizing vision experiences for patients at patient-preferred distances as part of prescribing glasses, or determining LAL adjustments. Some patients prefer optimized near vision, at distances of about 40 cm, others optimized distance vision at 6 meters, but in office settings it is more and more customary to optimize vision at intermediate distances, such as at 60 cm-70 cm. In a traditional optometrist lane, the measurement distances are fixed, whereas with the multi-channel subjective refractor 100 the optometrist can simulate the visual experience at any distance according to the patient's preference.

Figures 5, 6:
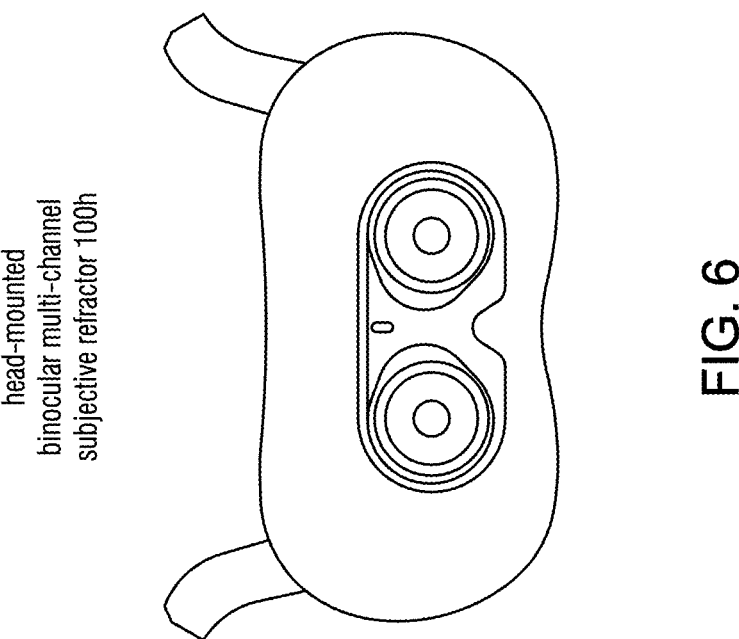
FIG. 5 shows a binocular multi-channel subjective refractor.
FIG. 6 shows a head mounted binocular multi-channel subjective refractor.

FIG. 5 shows that some embodiments of the multi-channel subjective refractor 100 can provide a refractor for each eye, thereby forming a binocular multi-channel subjective refractor 100b. Each of the individual multi-channel subjective refractors 100L and 100R for the left and right eyes, respectively, of this binocular refractor 100b can use or employ any of the previously described embodiments of the multi-channel subjective refractor 100.

FIG. 6 further shows that such a binocular multi-channel subjective refractor 100b can be implemented as a head-mounted binocular multi-channel subjective refractor 100h, which, again, can utilize any previously described embodiment of the individual multi-channel subjective refractor 100.

Figure 7:
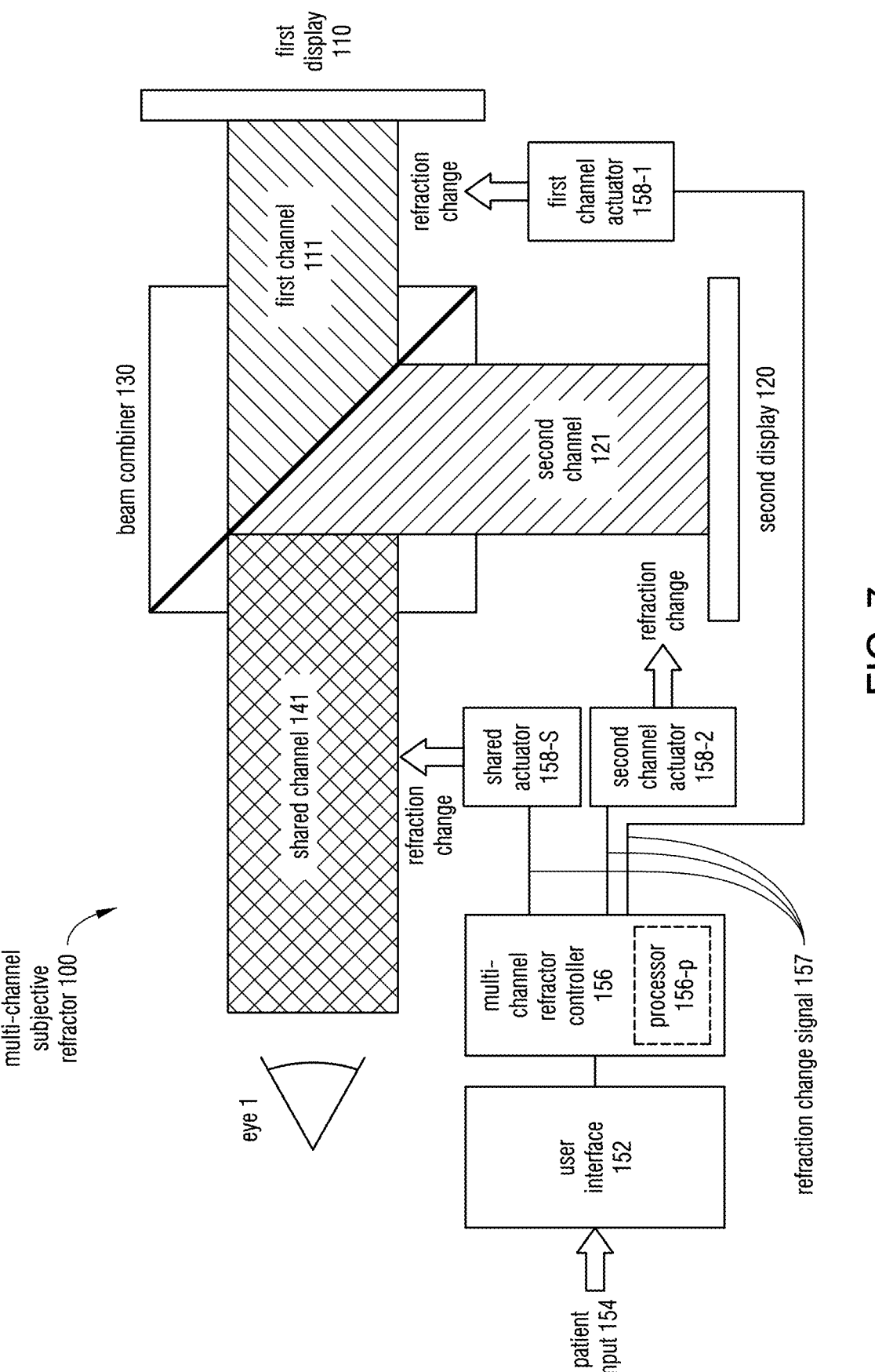
FIG. 7 shows an automated multi-channel subjective refractor.

FIG. 7 shows that the operation of the multi-channel subjective refractor 100 can be partially or fully automated. A few, or several, or all steps of the operation of such automated refractors 100 can be automated, and therefore can be carried out by a lesser trained technician, or possibly even by the patient herself. Naturally, such automation can further reduce the chair time, or demand on the optometrist's lane, and thus can have multiple beneficial effects on the optometry practice. Such automated refractors 100 enable the patient herself to explore the refraction parameter space away from the chair or lane, in a preparation or waiting area. This allows the patient to take all the time needed to repeatedly try out various refractions, possibly for longer periods and allow her eyes to accommodate to the presented refractions. Such unhurried, self-guided refraction measurements with the multi-channel subjective refractor 100 may increase the accuracy and reliability of the eventually chosen optimal refraction.

Some embodiments of such an automated multi-channel subjective refractor 100 may include an automated refraction control system to receive an input from the patient; and to change at least one of the first refraction 113 and the second refraction 123, in response to the patient input. In more detail, the multi-channel subjective refractor 100 may include a user interface 152 to receive a patient input 154; a multi-channel subjective refractor controller 156, to generate a refraction change signal 157 in response to the patient input 154; at least two of a shared actuator 158-S, a first channel actuator 158-1 and a second channel actuator 158-2, coupled to the multi-channel subjective refractor controller 156, to change a corresponding refraction in response to the refraction modification signal 157.

In an example of the operation, the multi-channel controller 100 may present the letter E with a first refraction 113 of 2.0 D, and with a second refraction 123 of 2.5 D for an eye 1, as shown in FIG. 4B, side by side, and the patient may be prompted to create a patient input 154 by indicating which letter is sharper. Having received this patient input 154, the multichannel refractor controller 156, or simply refractor controller 156, can generate a refraction change signal 157 to increase or to decrease the first or second refraction 113/123 presented to the patient.

The patient can generate the patient input 154 in many different ways. The patient input 154 can be verbal, i.e. saying out loud which is the sharper image, and the corresponding electric control input can be generated by the optometrist, or a technician, by selecting a refraction change on a graphical user interface of the user interface 152. In these semi-automated designs, the role of the refractor controller 156 is only to generate a refraction change signal 157 that corresponds to the entered refraction change. In other semi-automated embodiments, the user interface 152 can have dials, knobs, sliders, or any other types of input devices, and the patient can be prompted to turn a knob to create a refraction change command for the refractor controller 156. In this case, the refractor controller 156 again only generates a refraction change signal 157 that corresponds to the refraction change command by the patient, to make the actuators 158-S, 158-1 and 158-2 to carry out the corresponding refraction changes.

In other, fully automated designs, the user interface 152 can be a voice recognition system that understands the verbal patient input 154 and translates it for the refractor controller 156. The patient input can be only which image 110i or 120i appeared sharper for the patient, but may not specify a refraction change value. In these designs, the refractor controller 156 can have a (search) algorithm installed in a processor, or computer, 156-p that actually determined what refraction change is most reasonable given the patient input 154.

In any of the above embodiments, the user interface 152 can be one of a graphic user interface, a voice recognition and control interface, a motion sensor, and an at least partially mechanical interface, including one of a slider, a knob, or a switch.

As discussed, the automated multi-channel subjective refractor 100 can be partially or fully automated. In non-automated traditional refractors, the refraction change is typically created by mechanical changes, e.g., by moving lenses in or out of the optical pathway mechanically.

In partially (semi-) automated multi-channel subjective refractors 100, the refraction change can be partially electronic. For example, the user interface 152 can be a voice recognition system, and the refractor controller 156 is tasked to convert the voice-recognized command into the electronic refraction change signals 157. These refraction change signals 157 eventually can actuate an electromotor that causes the translation of the first or second displays 110/120 along their translational stages 115/125, or move the movable lenses 114/124/144, or rotate the lenses of the stokes lens 116/126/146.

In some embodiments, the multi-channel subjective refractor 100 can be fully automated by including the optional processor 156-p, to scan a relevant refraction parameter space efficiently by executing a search algorithm;

and to change the corresponding refraction according to the search algorithm. The refraction parameter space can include at least three dimensions: the defocus/sphere/optical power, the magnitude of the cylinder, and the direction of the cylinder. The latter two can be reparametrized as the cylinder in the 0 degree and in the 45 degree direction, or in the x and y direction. In more complex embodiments of the multi-channel subjective refractor 100, the refraction search space can be spanned by more than three dimensions.

Including the processor 156-p can be very useful, because the mere patient input 154 that, e.g., "the first image 110i with the first refraction 113 appeared sharper than the second image 120i with the second refraction 123", does not determine unequivocally how to change the refraction. There can be more than one refraction changes that are well-motivated by the same patient input 154. As it is well known, naïve "brute force" scanning search algorithms can be very inefficient. There are now textbooks dedicated to how to accelerate and to improve the efficiency of search algorithms. The search algorithm, coded and stored in a computer-readable medium, in conjunction with the processor 156-p can be any of these optimization algorithms, such as convex optimization, conjugate gradient methods, genetic codes, neural network codes, linear, binary, hashing algorithms, artificial-intelligence-based algorithms, or any other search algorithm. Such search algorithms can change two or even three refraction parameters simultaneously, which enable search process on the multi-channel subjective refractor 100 to converge to the optimal refraction much faster than the naïve scanning methods.

In some embodiments, the multi-channel subjective refractor 100 can also potentially present a series of letters at different resolutions at the end of the refraction process to the patient to read off (or type) using the determined refraction, in order to get another measure of the patient's best corrected visual acuity.

FIG. 8 shows a method 200 of operating the multi-channel subjective refractor 100. The method 200 can include the steps of:

generating 210 a first image 110i with a first refraction 113 and a second image 120i with a second refraction 123 with the multi-channel subjective refractor 100;

presenting 220 the first image 110i with the first refraction 113 and the second image 120i with the second refraction 123 simultaneously for an eye 1 of a patient by the multi-channel subjective refractor 100; and prompting 230 the patient to identify the sharper of the first image 110i and the second image 120i.

This description of the method steps already captures a distinguishing factor of the refractor 100 and the method 200: that the first and second images 110i and 120i are presented in parallel, simultaneously for the patient.

The generating step 210 and the presenting step 220 can be carried out by the various embodiments of the multi-channel subjective refractor 100, as described in FIGS. 1-7 above. The prompting step 230 can be carried out either verbally by a medical technician or a doctor, or in an automated fashion, e.g. by a voice command generated by the multi-channel subjective refractor 100 itself. As is reasonable, in either of these cases, the patient should be given the necessary time to make a considered choice.

FIG. 9 shows in some detail that in the method 200 the generating 210 can comprise generating 210-1 the first image 110i with a first display 110; generating the second image 120i with a second display 120; refracting 210-2 the first image 110i by a first channel 111 with a first channel refraction 112; refracting the second image 120i by a second channel 123 with a second channel refraction 112; receiving 210-3 and combining the first image 110i and the second image 120i by a beam combiner 130; receiving 210-4 the first image 110i and the second image 120i from the beam combiner 130 by a shared channel 141; refracting 210-5, by a combination of the shared channel 141 with the first channel 111, the first image 110i with the first refraction 113; refracting, by a combination of the shared channel 141 with the second channel 121, the second image 120i with the second refraction 123; and presenting 220 the first image 110i with the first refraction 113 and the second image 120i with the second refraction 123 to an eye 1 simultaneously.

In some embodiments of the method 200 the first channel refraction 112 comprises at least one of a first channel defocus and a first channel cylinder; the second channel refraction 122 comprises at least one of a second channel defocus and a second channel cylinder; the first refraction 113 comprises at least one of a first defocus and a first cylinder; and the second refraction 123 comprises at least one of a second defocus and a second cylinder.

Some embodiments of the method 200 are related to FIGS. 2A-B and can comprise refracting the first image 110i by the first channel 111 with the first defocus and the first cylinder; and refracting the second image 120i by the second channel 121 with the second defocus and the second cylinder; without refracting the first image 110i and the second image 120i by the shared channel 141. In these methods 200, the first channel 111 can comprise at least one of a first movable lens 114, a first variable power lens, a first deformable mirror, a first phase modulator, and a first translational stage 115 to move the first display 110, to refract the first image 110i with the first defocus; and a first stokes lens 116, to refract the first image with the first cylinder; and the second channel 121 can comprise at least one of a second movable lens 124, a second variable power lens, a second deformable mirror, a second phase modulator, and a second translational stage 125 to move the second display 120, to refract the second image 120i with the second defocus; and a second stokes lens 126, to refract the second image 120i with the second cylinder. The relationships between the first/second channel defocus and cylinder and the first/second defocus and cylinder are shown in the refraction table in FIG. 2B and above.

FIGS. 3A-F show that other embodiments of the method 200 can comprise refracting the first image 110i and the second image 120i by the shared channel 141 with a shared refraction 143 that includes at least one of a shared defocus SD and a shared cylinder SC; wherein the shared channel 141 comprises at least one of a shared movable lens 144, a shared variable power lens, a shared deformable mirror, or a shared phase modulator, to refract the first image 110i and the second image 120i with the shared defocus SD; and a shared stokes lens 146, to refract the first image 110i and the second image 120i with the shared cylinder SC. These embodiments of the method 200 can further comprise the following.

(1) Refracting the first image 110i by the first channel 111 with the first channel defocus CD1 that combines with the shared defocus SD to create the first defocus D1, wherein the first channel 111 comprises at least one of a first movable lens 114, a first variable power lens, a first deformable mirror, a first phase modulator, or a first translational stage 115 to move the first display 110; and (2) Refracting the first image 110i by the first channel 111 with the first channel cylinder CC1 that combines with the shared cylinder SC to create the first cylinder C1 using a first stokes lens 116; or (3) Refracting the second image 120i by the second channel 121 with the second channel defocus CD2 that combines with the shared defocus SD to create the second defocus D2, wherein the second channel 121 comprises at least one of a second movable lens 124, a second variable power lens, a second deformable mirror, a second phase modulator, or a second translational stage 125 to move the second display 120; and (4) Refracting the second image 120i by the second channel 121 with the second channel cylinder CC2 that combines with the shared cylinder SC to create the second cylinder C2, using a second stokes lens 126.

In some embodiments of the method 200 one of the refracting by the first channel 111 and refracting by the second channel 121 may not take place. In these embodiments, the shared defocus SD and the shared cylinder SC, refracted by the shared channel 141 is in fact the entire refraction of the channel which has no channel refraction.

As discussed before, one of the advantages of using the method 200 to operate the multi-channel subjective refractor 100 is that in this method the wide range of refractions can be implemented only in the shared channel 141, and the individual channels 111 and 121 may be used only to refract the corresponding images by a small, differential amount. Accordingly, in some embodiments, refracting by one of the channels may include refracting by less than two diopters in at least one of the first channel defocus CD1, the first channel cylinder CC1, the second channel defocus CD2 and the second channel cylinder CC2.

In some embodiments, the numerous degrees of freedom of the multi-channel subjective refractor 100 enable the method 200 for independently adjusting the first refraction 113 and the second refraction 123 by the first channel 111, the second channel 121 and the shared channel 141.

As FIGS. 4A-B show, an important aspect of the multi-channel subjective refractor 100 and the method 200 is that the latter includes presenting the first image 110i with the first refraction 113 and the second image 120i with the second refraction 123 simultaneously in one of an up-down image pair, a side-by-side image pair, and an image pair. In some embodiment, the method 200 can further include presenting one or more additional images with corresponding refractions simultaneously for the eye using one or more additional channels.

FIGS. 5-6 show that some embodiments can have a multi-channel subjective refractor 100 for each eye, thereby forming a binocular multi-channel subjective refractor 100b. This binocular multi-channel subjective refractor can be implemented as a head-mounted binocular multi-channel subjective refractor 100h.

FIG. 7 shows that some embodiments of the method 200 can further comprise receiving 240 the patient input 154 from the patient via the user interface 152; and changing 250 at least one of the first refraction 113 and the second refraction 123 in response to the patient input 154 via a multi-channel subjective refractor controller 100. The receiving 240 can include receiving the patient input 154 via the user interface 152 directly from the patient, or indirectly by the patient conveying the input to a medical professional for entering it into the user interface 152. As discussed above, in some exemplary indirect embodiments, the patient can identify verbally which image and refraction is sharper, and a medical technician, or the optometrist OD can enter the patient input 154 into the user interface 152. In direct embodiments the user interface 152 can include a voice command unit that recognizes the statement by the patient. Or there can be an electro-mechanical button, switch, slider, or knob at the hand of the patient, to select the sharper image and possibly, to command the multi-channel subjective refractor 100 to increase or decrease parameters of the refraction, such as to increase the defocus, or optical power of the refraction.

In some embodiments, the changing 250 can include generating a refraction change signal 157 by the multi-channel subjective refractor controller 156 in response to the patient input 154; and changing at least one of the first refraction 113 and the second refraction 123 in response to the refraction change signal 157 by at least one of the shared actuator 158-S, the first channel actuator 158-1 and the second channel actuator 158-2, coupled to the multi-channel subjective refractor controller 156.

In some embodiments, the method 200 can be semi-automated, wherein the patient 154 input includes a new refraction value for at least one of the first refraction 113 and the second refraction 123; and the generating the refraction change signal 157 includes translating the entered new refraction value into the refraction change signal 157 by the refraction controller 156.

Other embodiments of the method 200 can be automated, wherein the patient input 154 does not include a new refraction value for at least one of the first refraction 113 and the second refraction 123; the multi-channel refraction controller 156 comprises a processor **156-*p*; and the generating the refraction change signal 157 includes generating the refraction change signal 157 by performing a search algorithm to identify a new refraction value from the patient input by the processor 156-*p***.

FIG. 8 shows that the method 200 typically includes repeating 260 the generating 210, the presenting 220, the prompting 230, the receiving 240, and the changing 250 steps iteratively until either the first refraction 113 or the second refraction 123 is identified as optimal. This iterative process is much faster, more precise, and inflicts less mental fatigue with the here-described parallel-presenting multi-channel subjective refractor 200 than with traditional, sequentially-presenting refractors.

Some embodiments of the method 200 eliminate one more potential source of subjective bias by adding a step of exchanging a spatial presentation of the first image 110*i* with the first refraction 113 and the second image 120*i* with the second refraction 123 after the optimal refraction has been identified; and testing whether the optimal refraction remained optimal after the exchange. In an example, if at the end of the iterative search process the patient states that the first image 110*i*, shown with the first refraction 113 spatially above the second image 120*i* is the optimal, then the two images and refractions can be exchanged, followed by re-presenting the first image 110*i* with the first refraction 113 spatially below the second image 120*i* with the second refraction 123. A possible way to do it is to exchange both the images and the refractions, making the first image 110*i* the second image 120*i*, and the first refraction 113 the second refraction 123, and vice versa, and then prompt the patient to again identify the optimal refraction. Other, equivalent designs can achieve the same verification or confirmation.

Referring back to the duochrome tests, in some embodiments of the method 200 the generating 210 can comprise generating the first image 110*i* and the second image 120*i* with approximately the same background color.

In some embodiments of the method 200, the generating 210 can comprise generating the first image 110*i* with the first refraction 113 and the second image 120*i* with the second refraction 123 that is different from the first refraction 113.

Finally, it is mentioned that for patients who have more accommodation in their eyes, the method 200 can be used with appropriate adjustments.

While this document contains many specifics, details and numerical ranges, these should not be construed as limitations of the scope of the invention and of the claims, but, rather, as descriptions of features specific to particular embodiments of the invention. Certain features that are described in this document in the context of separate embodiments can also be implemented in combination in a single embodiment. Conversely, various features that are described in the context of a single embodiment can also be implemented in multiple embodiments separately or in any suitable subcombination. Moreover, although features may be described above as acting in certain combinations and even initially claimed as such, one or more features from a claimed combination can in some cases be excised from the combination, and the claimed combination may be directed to another subcombination or a variation of a subcombinations.

The invention claimed is:

1. A multi-channel subjective refractor, comprising:
a first display to generate a first image;
a second display to generate a second image;
a first channel to refract the first image with a first channel refraction;
a second channel to refract the second image with a second channel refraction;
a beam combiner to receive and to combine the first image and the second image; and
a shared channel,
to receive the first image and the second image from the beam combiner;
to refract, in combination with the first channel, the first image with a first refraction;
to refract, in combination with the second channel, the second image with a second refraction; and
to present the first image with the first refraction and the second image with the second refraction to an eye simultaneously, wherein: the first channel refraction comprises at least one of a first channel defocus and a first channel cylinder; the second channel refraction comprises at least one of a second channel defocus and a second channel cylinder; the first refraction comprises at least one of a first defocus and a first cylinder; and the second refraction comprises at least one of a second defocus and a second cylinder.

2. The multi-channel subjective refractor of claim 1, wherein:
the first channel and the second channel share an optical aperture after being combined by the beam combiner.

3. The multi-channel subjective refractor of claim 1, wherein:
the shared channel is not configured to refract the first image and the second image;
the first channel is configured to refract the first image with the first defocus and the first cylinder; and
the second channel is configured to refract the second image with the second defocus and the second cylinder.

4. The multi-channel subjective refractor of claim 3, wherein:
the first channel comprises at least one of a first movable lens, a first variable power lens, a first deformable mirror, a first phase modulator, and a first translational stage to move the first display, to refract the first image with the first defocus; and a first stokes lens, to refract the first image with the first cylinder; and the second channel comprises at least one of a second movable lens, a second variable power lens, a second deformable mirror, a second phase modulator, and a second translational stage to move the second display, to refract the second image with the second defocus; and a second stokes lens, to refract the second image with the second cylinder.

5. The multi-channel subjective refractor of claim 1, wherein:

the shared channel is configured to refract the first image and the second image with a shared refraction that includes at least one of a shared defocus and a shared cylinder; and the shared channel comprises at least one of a shared movable lens, a shared variable power lens, a shared deformable mirror, or a shared phase modulator, to refract the first image and the second image with the shared defocus; and a shared stokes lens, to refract the first image and the second image with the shared cylinder.

6. The multi-channel subjective refractor of claim 5, wherein:

the first channel comprises at least one of a first movable lens, a first variable power lens, a first deformable mirror, a first phase modulator, or a first translational stage to move the first display, to refract the first image with the first channel defocus that combines with the shared defocus to create the first defocus; and a first stokes lens, to refract the first image with the first channel cylinder that combines with the shared cylinder to create the first cylinder; or the second channel comprises at least one of a second movable lens, a second variable power lens, a second deformable mirror, a second phase modulator, or a second translational stage to move the second display, to refract the second image with the second channel defocus that combines with the shared defocus to create the second defocus; and a second stokes lens, to refract the second image with the second channel cylinder that combines with the shared cylinder to create the second cylinder.

7. The multi-channel subjective refractor of claim 5, wherein:

at least one of the first channel defocus, the first channel cylinder, the second channel defocus and the second channel cylinder are less than two diopters.

8. The multi-channel subjective refractor of claim 5, wherein:

one of the first channel and the second channel is not configured to refract the corresponding first image or second image.

9. The multi-channel subjective refractor of claim 1, wherein:

the first channel, the second channel and the shared channel are configured to enable an independent adjustment of the first refraction and the second refraction.

10. The multi-channel subjective refractor of claim 1, wherein:

the multi-channel subjective refractor is configured to present the first image with the first refraction and the second image with the second refraction simultaneously in one of an up-down image pair, a side-by-side image pair, and an image pair.

11. The multi-channel subjective refractor of claim 1, wherein:

the first image and the second image are the same, and include one or more letters of an eye chart, of a Snellen chart, of an army target, or a figure of an examination chart.

12. The multi-channel subjective refractor of claim 1, comprising:

one or more additional channels, configured to present one or more additional images with corresponding refractions simultaneously for the eye.

13. The multi-channel subjective refractor of claim 1, comprising:

a multi-channel subjective refractor for each eye, thereby forming a binocular multi-channel subjective refractor.

14. The multi-channel subjective refractor of claim 13, wherein:

the binocular multi-channel subjective refractor is implemented as a head-mounted binocular multi-channel subjective refractor.

15. The multi-channel subjective refractor of claim 1, comprising:

an automated refraction control system to receive an input from the patient; and to change at least one of the first refraction and the second refraction, in response to the patient input.

16. The multi-channel subjective refractor of claim 15, comprising:

a user interface to receive the patient input;

a multi-channel subjective refractor controller to generate a refraction change signal in response to the input; and at least two of a shared actuator, a first channel actuator and a second channel actuator, coupled to the multi-channel subjective refractor controller, to change a corresponding refraction in response to the refraction change signal.

17. The multi-channel subjective refractor of claim 15, wherein:

the user interface is one of a graphic user interface, a voice recognition and control interface, a motion sensor, and an at least partially mechanical interface, including one of a slider, a knob, or a switch.

18. The multi-channel subjective refractor of claim 15, wherein:

the multi-channel subjective refractor controller includes a processor to scan a relevant refraction parameter space efficiently by executing a search algorithm; and to change the corresponding refraction according to the search algorithm.

19. The multi-channel subjective refractor of claim 1, wherein:

the first display generates the first image with approximately the same background color as the second display generates the second image.

20. The multi-channel subjective refractor of claim 1, wherein:

the first refraction is different from the second refraction.

* * * * *